United States Patent
Ning et al.

(10) Patent No.: US 11,541,202 B2
(45) Date of Patent: Jan. 3, 2023

(54) METHOD, SYSTEM AND DEVICE FOR ASSISTED SLEEP

(71) Applicant: Deep Sleep Boost, Inc., Mesa, AZ (US)

(72) Inventors: Kelvin Ning, Phoenix, AZ (US); Blake Sakran, Smithton, IL (US)

(73) Assignee: DEEP SLEEP BOOST, INC., Mesa, AZ (US)

( * ) Notice: Subject to any disclaimer, the term of this patent is extended or adjusted under 35 U.S.C. 154(b) by 0 days.

(21) Appl. No.: 17/073,116

(22) Filed: Oct. 16, 2020

(65) Prior Publication Data

US 2021/0178112 A1 Jun. 17, 2021

Related U.S. Application Data

(63) Continuation of application No. PCT/US2019/029419, filed on Apr. 26, 2019.

(60) Provisional application No. 62/664,416, filed on Apr. 30, 2018.

(51) Int. Cl.
*A61M 21/02* (2006.01)
*A61B 5/00* (2006.01)
*A61M 21/00* (2006.01)

(52) U.S. Cl.
CPC ............ *A61M 21/02* (2013.01); *A61B 5/4812* (2013.01); *A61M 2021/0022* (2013.01); *A61M 2021/0027* (2013.01)

(58) Field of Classification Search
CPC .......... A61M 21/02; A61M 2021/0022; A61M 2021/0027; A61M 2021/0083; A61B 5/4812
See application file for complete search history.

(56) References Cited

U.S. PATENT DOCUMENTS

| | | | |
|---|---|---|---|
| 8,755,879 B2 | 6/2014 | Hang et al. | |
| 9,730,632 B1 | 8/2017 | Kayyali et al. | |
| 10,232,139 B1 | 3/2019 | Hang et al. | |
| 2014/0057232 A1 | 2/2014 | Wetmore et al. | |
| 2015/0258301 A1* | 9/2015 | Trivedi | A61B 5/0024 600/28 |
| 2016/0136383 A1 | 5/2016 | Franceschetti et al. | |
| 2017/0143254 A1* | 5/2017 | Bell | A61B 5/0004 |
| 2018/0078733 A1* | 3/2018 | Freed | A61B 5/0205 |
| 2020/0178887 A1* | 6/2020 | Correa Ramirez | A61B 5/4806 |

FOREIGN PATENT DOCUMENTS

CN 201580320 U * 9/2010

OTHER PUBLICATIONS

Ngo et al. ("Induction of slow oscillations by rhythmic acoustic stimulation". Journal of Sleep Research, 22: 22-31. https://doi.org/10.1111/j.1365-2869.2012.01039.x) (Year: 2013).*

(Continued)

*Primary Examiner* — Kaylee R Wilson
(74) *Attorney, Agent, or Firm* — Knobbe Martens Olson & Bear LLP

(57) ABSTRACT

The methods, systems and devices provided herein relate to sleep-aid. Some embodiments include a vibration source and/or a sound source. In some embodiments, the vibration source and/or sound source emit vibrations and/or sounds that stimulate a subject's vagus nerve, or another nerve, to induce sleep or relaxation in the subject.

12 Claims, 17 Drawing Sheets

(56) References Cited

OTHER PUBLICATIONS

International Search Report and Written Opinion, dated Aug. 15, 2019, 11 pages.
John-Olof Nilsson, Amit K Gupta, and Peter Hande, *Footmounted inertial navigation made easy,* 2014 International Conference on Indoor Positioning and Indoor Navigation, Oct. 27-30, 2014, www.openshoe.org/wp-content/uploads/2014/09/made_easy.pdf.

* cited by examiner

METHOD, SYSTEM AND DEVICE FOR ASSISTED SLEEP

INCORPORATION BY REFERENCE TO RELATED APPLICATION

Any and all priority claims identified in the Application Data Sheet, or any correction thereto, are hereby incorporated by reference under 37 CFR 1.57. This application is a continuation, under 35 U.S.C. § 120, of International Patent Application No. PCT/US2019/029419, filed Apr. 26, 2019 under the Patent Cooperation Treaty (PCT), which was published by the International Bureau in English on Nov. 7, 2019, which designates the United States and claims the benefit of U.S. Provisional Application No. 62/664,416, filed Apr. 30, 2018. Each of the aforementioned applications is incorporated by reference herein in its entirety, and each is hereby expressly made a part of this specification.

FIELD

The methods, systems and devices provided herein relate to sleep-aid. Some embodiments include a vibration source and/or a sound source. In some embodiments, the vibration source and/or sound source emit vibrations and/or sounds. In some embodiments, the vibrations and/or sounds stimulate a subject's vagus nerve, or another nerve, to induce sleep or relaxation in the subject.

BACKGROUND

Many people have trouble sleeping, are in need of aid in relaxation, or have difficulty in waking from deep sleep. Some types of sleep tracking and waking optimization systems and methods are disclosed in U.S. Pat. No. 8,755,879, which is hereby incorporated by reference in its entirety.

SUMMARY

Systems, devices, and methods to address one or more problems related to relaxation, sleeping and waking are desirable.

In a first aspect, a sleep-aid device is provided. The sleep-aid device includes, for example, a speaker that generates white, pink or brown noise and a vibration motor that causes vibrations in a pillow when placed next to the pillow. In some embodiments, the vibrations in the pillow stimulate the vagus nerve of a subject when the subject rests her head on the pillow. In some embodiments, the sleep-aid device further includes one or more of a processor, a battery, an accelerometer, a memory, a means for communicating with a smartphone. In some embodiments, the means for communicating with a smartphone is wired. In some embodiments, the means for communicating with a smartphone is wireless. In some embodiments, the means for communicating with a smartphone is Bluetooth. In some embodiments, the sleep-aid device further includes a termination sequence activated by one or more of a predetermined timer, movement data, heart rate, and respiration data. In some embodiments, the sleep-aid device further includes one or more of Deep Sleep Boost™ and Gentle Wake-up™ technology. In some embodiments, the vibration motor further includes a strap that wraps around the pillow. In some embodiments, the strap wraps vertically around the middle of the pillow. In some embodiments, the strap wraps along a middle bottom of the pillow to the top of the pillow. Some embodiments include a plurality of accelerometers. In some embodiments, the plurality of accelerometers includes accelerometers arranged in a 2×2 matrix layout in relation to each other.

In a second aspect, a method for inducing sleep in a subject is provided. The method includes, for example, activating a device in or near a pillow, generating white, pink or brown noise through the device, and causing the device to produce pillow vibrations, thereby stimulating the subject's vagus nerve and inducing sleep in the subject.

In some embodiments, the method further includes connecting the device to a smartphone. In some embodiments, the connection of the device to a smartphone is wireless. In some embodiments, the method further includes controlling, via the smartphone, the white, pink or brown noise or the vibrations. In some embodiments, controlling the vibrations includes controlling the speed, strength, rhythm, repetition, or pattern of the vibrations. In some embodiments, controlling the white, pink or brown noise includes controlling the pitch, frequency, period, loudness, volume, amplitude, intensity, rhythm, timbre, tone, speed, strength, repetition, or pattern of the white, pink or brown noise. In some embodiments, stimulating the subject's vagus nerve decreases the subject's heart rate or respiration rate. Some embodiments include measuring the subject's respiration rate or heart rate with a plurality of accelerometers. Some embodiments include generating sleep entrainment beats. In some embodiments, the device uses one or more speakers to generate the sleep entrainment beats or use of haptic vibrations to create the same beat pattern.

In a third aspect, a system for inducing sleep in a subject is provided. The system includes, for example, a speaker that generates white, pink or brown noise, a pillow, and a vibration motor that causes vibrations in the pillow when placed next to the pillow. In some embodiments, the vibrations in the pillow stimulate the vagus nerve of a subject when the subject rests her head on the pillow.

In some embodiments, the system further includes a strap connecting the vibration motor to the pillow. In some embodiments, the strap is wrapped along a middle bottom of the pillow to the top of the pillow. In some embodiments, the strap is wrapped vertically around the pillow in relation to the subject's neck.

In a fourth aspect, a system for inducing sleep in a subject is provided. The system includes, for example, a speaker that generates white, pink or brown noise, a pillow having a first side configured to receive a subject's head and a second side opposite the first side, an accelerometer positioned on the first side of the pillow, and a vibration motor inside or next to the pillow. In some embodiments, vibrations may stimulate the vagus nerve of a subject when the subject rests her head on the first side of the pillow.

In some embodiments, the system further includes a strap connecting the vibration motor or the accelerometer to the pillow. In some embodiments, the strap wraps along the middle bottom of the pillow to the top of the pillow. In some embodiments, the strap is wrapped vertically around the center of the pillow so as to be substantially aligned with the subject's head.

In a fifth aspect, a system for inducing sleep in a subject is provided. The system may include, for example, a speaker, a pillow having a first side configured to receive a subject's head and a second side opposite the first side, a plurality of accelerometers arranged in a 2×2 matrix formation on the second side of the pillow, and a vibration motor. In some embodiments, the vibration motor is configured to produce vibrations in the pillow when placed next to or inside the pillow. In some embodiments, the vibrations stimulate the vagus nerve of a subject when the subject rests her head on the first side of the pillow. In some embodiments, the speaker is configured to generate white, pink or brown noise.

In some embodiments, the system further includes a strap connecting the vibration motor or the plurality of accelerometers to the pillow. In some embodiments, the strap wraps along the middle bottom of the pillow to the top of the pillow. In some embodiments, the strap is wrapped around an outside perimeter of the pillow.

BRIEF DESCRIPTION OF THE DRAWINGS

Features of the present disclosure will become more fully apparent from the following description and appended claims, taken in conjunction with the accompanying drawings. It will be understood that these drawings depict only certain embodiments in accordance with the disclosure and, therefore, are not to be considered limiting of its scope; the disclosure will be described with additional specificity and detail through use of the accompanying drawings. An apparatus, system or method according to some of the described embodiments can have several aspects, no single one of which necessarily is solely responsible for the desirable attributes of the apparatus, system or method. After considering this discussion, and particularly after reading the section entitled "Detailed Description of Certain Inventive Embodiments" one will understand how illustrated features serve to explain certain principles of the present disclosure.

DETAILED DESCRIPTION OF CERTAIN INVENTIVE EMBODIMENTS

Figure 1:
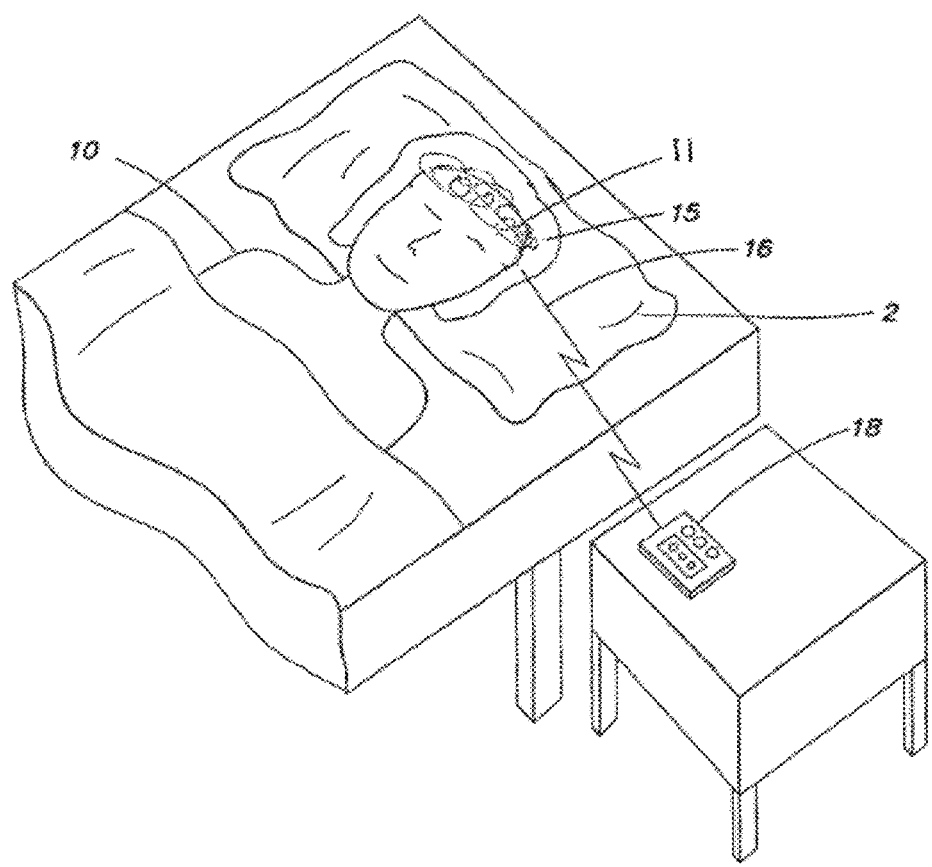
FIG. 1 is a perspective view of a user using an embodiment of a device with Deep Sleep Boost™ (DSB) and/or Gentle Wake-up™ (GWU) technology.

Some embodiments of the methods, systems and devices provided herein relate to sleep-aid. Some embodiments include a vibration source and/or a sound source. In some embodiments, the vibration source emits vibrations that stimulate a subject's vagus nerve to induce sleep or relaxation in the subject. In some embodiments, the sound source emits sounds that aid in inducing sleep or relaxation in the subject.

It will be readily understood that the aspects of the present disclosure, as generally described herein, can be arranged, substituted, combined, separated, and designed in a wide variety of different configurations, all of which are explicitly contemplated herein.

Unless defined otherwise, technical and scientific terms used herein have the same meaning as commonly understood by one of ordinary skill in the art to which the present disclosure belongs. All patents, applications, published applications and other publications referenced herein are expressly incorporated by reference in their entireties unless stated otherwise. For purposes of the present disclosure, the following terms are defined below.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. When a value is preceded by the term about, the component is not intended to be limited strictly to that value, but it is intended to include amounts that vary from the value.

Throughout this specification, unless the context requires otherwise, the words "comprise," "comprises," and "comprising" will be understood to imply the inclusion of a stated step or element or group of steps or elements but not the exclusion of any other step or element or group of steps or elements.

As used herein, a "subject" or a "patient" refers to an animal that is the object of treatment, observation or experiment. "Animal" comprises cold- and warm-blooded vertebrates and invertebrates such as fish, shellfish, reptiles and, in particular, mammals. "Mammal" comprises, without limitation, mice, rats, rabbits, guinea pigs, dogs, cats, sheep, goats, cows, horses, primates, such as monkeys, chimpanzees, and apes, and, in particular, humans. In some alternatives, the subject is human.

Stages of sleep including REM, light sleep, and deep sleep, described herein (see FIG. 12, for example) are understood as used in the art. For example, in some embodiments deep sleep is understood to refer to slow-wave sleep (SWS) a phase of sleep with slow wave brain activity (for example with a frequency range of 0.5-2 Hz) and low physical movement. In some embodiments, SWS includes two separate sleep stages: N3 which has 20-50% delta wave activity, and N4 which has more than 50% delta wave activity. In some embodiments, SWS includes both N3 and N4 in a single stage referred to as deep sleep. In some embodiments, SWS or deep sleep includes a period of sleep (such as 30 seconds or more) of 20% or more slow-wave (delta) sleep.

Some embodiments disclosed herein relate to selecting a subject or patient in need. In some embodiments, a patient is selected who is in need of therapy, treatment, amelioration, inhibition, progression, prophylaxis, or improvement related to sleep and/or relaxation. In some embodiments, a patient is selected who has a sleep disorder, or has difficulty sleeping or relaxing. Such identification or selection of said subjects or patients in need can be made through clinical and/or diagnostic evaluation or may be made through self-evaluation. In some embodiments, a subject is selected who does not have difficulty sleeping, but who wishes to improve the quality of her sleep. Examples of sleep disorders include bruxism, catathrenia, delayed sleep phase disorder, advanced sleep phase disorder, non-24-hour sleep-wake disorder, irregular sleep wake rhythm, shift work sleep disorder, hypopnea syndrome, idiopathic hypersomnia, insomnia disorder (primary insomnia), Kleine-Levin syndrome, narcolepsy, night terror, pavor nocturnus, sleep terror disorder, nocturia, parasomnias, periodic limb movement disorder (PLMD), rapid eye movement sleep behavior disorder (RBD), restless legs syndrome (RLS), sleep apnea, sleep paralysis, sleepwalking or somnambulism, and somniphobia. Some embodiments include diagnosing the sleep disorder. Treating the sleep disorder with any of the devices, methods, or systems described herein.

Some embodiments include combining use of the device, method, or system with another form of treatment for a sleep disorder. For example, the device, method or system can be combined with a drug therapy for treatment of a sleep disorder. Such drug therapies include but are not limited to dopamine agonists (e.g., carbidopa/levodopa, bromocriptine, ropinirole, rotigotine, pramipexole) used to treat restless legs syndrome and periodic limb movement disorder, benzodiazepines (e.g., clonazepam, diazepam, temazepam, estazolam, alprazolam, lorazepam) used to treat parasomnias, bruxism, and short term insomnia, melatonin receptor stimulators (e.g., ramelteon) used to treat insomnia, opiates (e.g., codeine, oxycodone, methadone, dihydromorphone) used to treat restless legs syndrome that will not respond to other therapies or is present in pregnancy, anticonvulsants (e.g., carbamazepine, valproate, gabapentin enacarbil, pregabalin) used to treat nocturnal eating syndrome, restless legs syndrome, periodic limb movement disorder and insomnia related to bipolar disorder, anti-narcoleptics (e.g., modafinil, methylphenidate, sodium oxybate) used to treat narcolepsy and sleep apnea, and orexin receptor antagonists (e.g., suvorexant) used to regulate the sleep-wake cycle. The device, method or system can also be combined with natural sleep aids or supplements, e.g., melatonin, valerian root, magnesium, lavender, passion flower, glycine, tryptophan, gingko biloba, L-theanine, and kava.

The systems, devices, and methods described herein are intended to help users fall asleep. Some embodiments include a pillow insert wirelessly connected to a smartphone for input and control. In some embodiments, a device is placed within a pillow case, on top or under a pillow, in a pillow, or alternatively placed on a sheet, mattress pad, or on or in a mattress underneath the pillow. Some embodiments include a pillow topper. Some embodiments include a combination of both white, pink or brown noise and vagus nerve stimulation. White noise is broadly spread across the sound spectrum, including low-frequency, midrange, and high-frequency sounds, e.g., noise where the spectral density (power per Hertz) is even throughout all audible frequencies. It can be compared to the sound of a waterfall with water falling at different speeds and hitting different surfaces. Pink noise is louder at the low-frequency end of the spectrum and softer at the high end. The sound of light to medium rainfall is an example of pink noise. Brown noise is even deeper, even stronger than pink noise at the low end without the high frequency sounds of white and pink noise, it can sound similar to the low roar of an ocean or rumble of a thunderstorm.

Some embodiments include speakers that are placed within the pillow insert (or mattress insert, or in an insert or directly at any convenient location close to the user (e.g., a nightstand, headboard, or the like)) to play a variety of noises that can be selected by the user via their connected phone application. In some embodiments, based on a combination of signals, the white, pink or brown noise sound initiates a termination sequence (for example, a tapering volume). In some embodiments, these combinations of signals include a predetermined timer, movement data, heart rate, and respiration rate.

In some embodiments, along with white, pink or brown noise, the pillow insert provides vagus nerve stimulation. The vagus nerve is the tenth cranial nerve and interfaces with parasympathetic control of the heart, lungs, and digestive tract. The vagus nerves are paired but are normally referred to in the singular. The vagus nerve is the longest nerve of the autonomic nervous system in the human body. Upon leaving the medulla oblongata between the pyramid and the inferior cerebellar peduncle, the vagus nerve extends through the jugular foramen, then passes into the carotid sheath between the internal carotid artery and the internal jugular vein down to the neck, chest, and abdomen, where it contributes to the innervation of the viscera, reaching all the way to the colon. Besides giving some output to various organs, the vagus nerve comprises between 80% and 90% of afferent nerves mostly conveying sensory information about the state of the body's organs to the central nervous system. The right and left vagus nerves descend from the cranial vault through the jugular foramina, penetrating the carotid sheath between the internal and external carotid arteries, then passing posterolateral to the common carotid artery. The cell bodies of visceral afferent fibers of the vagus nerve are located bilaterally in the inferior ganglion of the vagus nerve (nodose ganglia).

The right vagus nerve gives rise to the right recurrent laryngeal nerve, which hooks around the right subclavian artery and ascends into the neck between the trachea and esophagus. The right vagus then crosses anterior to the right subclavian artery, runs posterior to the superior vena cava, descends posterior to the right main bronchus, and contributes to cardiac, pulmonary, and esophageal plexuses. It forms the posterior vagal trunk at the lower part of the esophagus and enters the diaphragm through the esophageal hiatus.

The left vagus nerve enters the thorax between left common carotid artery and left subclavian artery and descends on the aortic arch. It gives rise to the left recurrent laryngeal nerve, which hooks around the aortic arch to the left of the ligamentum arteriosum and ascends between the trachea and esophagus. The left vagus further gives off thoracic cardiac branches, breaks up into the pulmonary plexus, continues into the esophageal plexus, and enters the abdomen as the anterior vagal trunk in the esophageal hiatus of the diaphragm.

The vagus runs parallel to the common carotid artery and internal jugular vein inside the carotid sheath.

In some embodiments, stimulation of the vagus nerve or maintaining vagus nerve tone improves relaxation. In some embodiments, improved relaxation is achieved through vibrations (e.g., in the pillow or mattress) created by either sound or a vibration motor which conduct through the pillow or mattress, into the user's cranium, and passively to the vagus nerve.

In some embodiments, the white, pink or brown noise and vagus nerve stimulation is integrated with Deep Sleep Boost™ (DSB) and/or Gentle Wake-up™ (GWU) technology. In some embodiments, DSB and/or GWU is also embodied within a pillow case insert or on top of a mattress. Some embodiments utilize components provided to create the DSB and GWU, and include a processor, battery, vibration motor, speaker(s), accelerometer, memory, and/or ability to communicate (e.g. via Bluetooth) with a smartphone. Examples of DSB and GWU may be described below and in U.S. Pat. No. 10,232,139, which is hereby incorporated by reference in its entirety. In such technology, a pillow top or pillow cover device is provided comprising at least one non-invasive brain stimulator for stimulation of the brain at various selected frequencies; at least one sensor to monitor sleep; and a controller, wherein the at least one sensor provides the controller data regarding the state of sleep of the user; wherein the controller calculates brain activity indicating deep sleep slow-wave activity and activates the at least one brain stimulator to emit low frequency tones; wherein the tone emissions are monaural tones that are dynamic and are selected from the group consisting of timbre, pitch, rhythm, and volume. For example, acoustic stimulation at less than 1 Hz (notably 0.8 Hz) promotes slow wave activity in the brain and to enhance deep sleep. Dynamic monaural stimulation can be used to prevent habituation by constantly changing the composition of the sounds used for monaural stimulation. Such dynamic sound includes, but is not limited to the changing of timbre of the sound (e.g. from a pure tone to a cello-type sound and back), the pitch of the sound (e.g. varying from 250 Hz to 300 Hz over a 2-minute period); the rhythm of the sound (e.g. oscillating from 0.75 Hz to 0.9 Hz over a 20-second period); or the volume of the sound (e.g. oscillating from 30 dB to 35 dB over a 2-minute period).

Vibration

Some embodiments of the methods, systems and devices provided herein relate to one or more vibration sources. In some embodiments, the vibration source includes a mechanical device such as a motor. In some embodiments, the vibration source is a vibration motor. In some embodiments, the vibration source includes gears and/or other mechanical parts that produce friction and/or collide with each other to produce the vibration. In some embodiments, the device uses an oscillating weight vibrating motor. For example, the device may include a vibrating mini motor disc smaller than one inch across. The oscillating weight vibrating motor may include two wires to control and/or power the oscillating weight vibrating motor. The oscillating weight vibrating motor may include power provided from a battery or microcontroller pin. The oscillating weight vibrating motor uses, in some embodiments, 2V to 5V, or more, of current. The oscillating weight vibrating motor may include a resistor (100 to 1000 ohms, for example) in series to reduce the current draw/strength. In some embodiments, The oscillating weight vibrating motor includes dimension of about 10 mm diameter, about 2.7 mm thickness; a voltage of 2V-5V; a 5V current draw (100 mA, for example), a 4V current draw (80 mA, for example), a 3V current draw (60 mA, for example), a 2V current draw (40 mA, for example); about 11000 RPM at 5V; and/or a weight of about 0.9 gram. In some embodiments, the vibration source is electronic. In some embodiments, the vibration source is mechanical. In some embodiments, the vibration source is or includes a sound. In some embodiments, one or more vibration sources are combined.

In some embodiments, the vibration has variable features including but not limited to speed, strength, rhythm, and repetition. In some embodiments, the vibration is patterned. In some embodiments, the vibration is random or non-patterned. In some embodiments, the vibration is free vibration, forced vibration, and/or damped vibration. Some embodiments include a vibration pattern comprising a random interval, fixed duration, ascending strength vibration. Some embodiments include one or more combinations of vibration patterns such as fixed interval, variable duration, and fixed strength patterns. Some embodiments include a silent alarm that uses one or more of the vibration patterns described above. For example, the silent alarm may include a vibration pattern comprising a random interval, fixed duration, ascending strength vibration. In one example, the vibration strength was found to be much less effective as a silent alarm for waking subjects when played at a fixed strength, and users reported that the fixed vibration strength was either too weak to wake them up or too strong and jolted them awake, both of which were undesirable outcomes with regard to the silent alarm. A benefit of using a random vibration interval in the silent alarm is that it may avoid habituation to the stimulus, and fixing the duration may overcome technical limitations.

In some embodiments, the vibration source causes vibrations in another object when placed inside the other object. In some embodiments, the vibration source causes vibrations in another object when placed next to, on top of, or under the object (e.g., a pillow, mattress, nightstand, or headboard).

In some embodiments, the vibration source causes vibrations in a bedding item. In some embodiments, the vibration source causes vibrations in a pillow. In some embodiments, the vibration source causes vibrations in a mattress. For example, the vibration source may be placed on top of, under, or inside a pillow or mattress. In some embodiments, the vibration source causes vibrations in cushion, pad, foam pad, board, or other item. In some embodiments, the vibration source includes a form factor. In some embodiments, the form factor includes an insert placed on the top of a pillow. In some embodiments, the insert includes a strap, snap, zipper, button, velcro, tie, or other securing member. In some embodiments, the strap is wrapped around an outer perimeter of at least a portion of the pillow. In some embodiments, the strap is wrapped along the middle bottom of the pillow to the top of the pillow.

In some embodiments, the vibration source causes vibrations in a subject. In some embodiments, the subject is an animal. In some embodiments, the subject is a mammal (e.g., cat, dog, human). In some embodiments, the subject is a human. In some embodiments, the subject is a clinical patient. In some embodiments, the subject has difficulty falling asleep without a sleep aid device. In some embodiments, the subject does not have difficulty falling asleep.

In some embodiments, the vibration source causes vibrations directly in the subject. In some embodiments, the vibration source causes vibrations indirectly in the subject. In some embodiments, the vibration source causes vibrations indirectly in the subject by causing vibrations that travel from a bed, headboard, nightstand, or bedding item to the subject. The vibration source can also travel via bone conduction headphones.

In some embodiments, the vibration source causes vibrations in the subject's cranium or head. In some embodiments, the vibration source causes vibrations in the subject's neck, spine or back. In some embodiments, the vibration source causes vibrations in the subject's skin, blood vessels, bone, cartilage, muscle, ligaments, tendons, or tissue. In some embodiments, the vibration source causes vibrations in a nerve of the subject, or in the subject's nerves. In some embodiments, the nerve or nerves may include the subject's vagus nerve. In some embodiments, the vibration stimulates the nerve or nerves. For example, the vibration source may be placed within or next to a pillow to cause vibrations in the pillow. In some embodiments, the vibrations in the pillow stimulate the vagus nerve of a subject when the subject rests her head on the pillow. In some embodiments, the stimulation of the vagus nerve, or the stimulation of another nerve, decreases subject's heart rate and/or respiration rate. In some embodiments, the decrease in the subject's heart rate and/or respiration rate induces sleep or relaxation in the subject.

In some embodiments, the vibration source includes a form factor that fits around a person's back, neck and/or head. In some embodiments, the form factor includes an insert placed inside, next to, on the top of, or underneath a pillow. In some embodiments, the insert is sewn, glued, strapped or simply placed on, next to, inside, or underneath the pillow. The vibration source may contact the person by various means, and can generally be any shape.

In some embodiments, the insert includes a strap or other securing member as described elsewhere herein. In some embodiments, the vibration source has a strap or other securing member as described elsewhere herein. In some embodiments, the strap wraps around an outer perimeter of at least a portion of the pillow. In some embodiments, the strap wraps vertically around the middle or center of the pillow. In some embodiments, the vertical strap substantially aligns with or is parallel to a subject's neck or spine. In some embodiments, the placement of the strap in alignment with the subject's neck or spine allows vibrations from the vibration source to be centered on the subject's neck or spine. In some embodiments, the strap is in another orientation with the pillow, such as angled, diagonal, horizontal, or cross-wise with respect to a long surface of the pillow. In some embodiments, the strap bisects the pillow. In some embodiments, the strap bisects the pillow vertically, horizontally, diagonally, or in any other angle. In some embodiments, no strap attaches to the vibration source. In some embodiments, the vibration source has more than one strap. In some embodiments, the vibration source has one, two, three, four, five, six, seven, eight, nine, or ten straps, or any number therebetween. In some embodiments, at least one strap is for support, and/or aids in keeping the vibration source in place.

In some embodiments, the strap, the vibration source, and/or at least one accelerometer contacts a subject. In some embodiments, the contact is with the subject's head, neck, face, or back, or another part of the subject's body. In some embodiments, the contact is directly with an object associated with the subject such as the subject's clothing, bedsheets, bedcovering, chair or pillow, and the contact is indirectly with the subject's body. In some embodiments, the subject contacts the strap by lying on or across the strap.

In some embodiments, the strap contacts a pillow by laying on the pillow or by wrapping around an outer surface of the pillow. The strap or the vibration source may contact the pillow directly or indirectly. In some embodiments, the strap includes an adhesive or adherent. In some embodiments, the strap attaches to the pillow by the adhesive or adherent. Examples of adherents and/or adhesives include but are not limited to glue, Velcro, tape, hooks, loops, wires, polyvinyl acetate, cyanoacrylate, epoxy, polyurethane, and cement. In some embodiments, there is no adherent on the strap. In some embodiments, the pillow and/or strap includes a material such as cloth, plastic, leather, wool, cotton, polyester, nylon, foam, rubber, elastic, thread, rope, hemp or another material. In some embodiments, the pillow is fluffy or soft.

Sound

Some embodiments of the methods, systems and devices provided herein relate to a sound source. In some embodiments, the sound source generates a sound. In some embodiments, the sound has variable features including but not limited to pitch, frequency, period, loudness, volume, amplitude, intensity, timbre, tone, speed, strength, repetition, rhythm, and/or pattern.

In some embodiments, the sound includes white, pink or brown noise. In some embodiments, the white, pink or brown noise is a random signal having equal intensity at different frequencies, giving it a constant power spectral density. In some embodiments, the sound includes a recorded sound. In some embodiments, the sound includes a generated sound. In some embodiments, the white, pink or brown noise is generated by a mathematical equation or statistical property. In some embodiments, the white, pink or brown noise is Gaussian white, pink or brown noise, Poisson white, pink or brown noise, and/or Cauchy white, pink or brown noise. In some embodiments, the white, pink or brown noise is generated by a generalized mean-square derivative of the Wiener process or Brownian motion. In some embodiments, the white, pink or brown noise is generated by a musical instrument or is generated electronically.

In some embodiments, the sound includes ambient noise. In some embodiments, the sound includes music. In some embodiments, the sound includes a person's or animal's voice, singing, or nonmusical spoken word. In some embodiments, the sound includes one or more sounds of nature such as sounds produced by ocean waves, wind, a river, or a brook or stream. Some embodiments include a soundscape such as, for example, sounds of a rainforest, jungle, or beach. Some embodiments include noise cancellation sounds. For example, the noise cancellation sounds may include wavelengths that cancel sounds produced in an environment of a listener, where the listener the subject for which sleep is induced by a device, method, or system described herein.

In some embodiments, the sound source is or includes one or more speakers. In some embodiments, the speaker is inserted into, or placed next to a pillow, mattress, or bedding item. In some embodiments the speaker is part of a phone, cellphone, television, computer, radio, stereo, and/or other device. In some embodiments the speaker is includes a headphone speaker.

Some embodiments include speakers that deliver acoustic stimulation to enhance deep sleep. For example, stimulation at less than 1 Hz (notably 0.8 Hz) can promote slow wave activity in the brain.

In some embodiments, binaural stimulation is used to entrain for slow wave rhythms or beats via the superior olivary nucleus. In some embodiments, binaural simulation uses constant waveforms at different pitches to generate an efferent from the superior olivary nucleus. In some embodiments, the superior olive functions to localize the source of sounds, and in this method it is manipulated to create a rhythmic oscillation at the third frequency that the brain interprets as novel. In some embodiments, in normal conditions, the superior olivary nucleus only receives input from lower-level auditory pathways from the ears to determine the source of the sounds. In some embodiments, binaural stimulation using two different frequencies (e.g. 400 Hz and 410 Hz) to manipulate the superior olive to creates an efferent at a third frequency of 10 Hz that then entrains the brain. In some embodiments, this manipulation of the superior olive keeps the stimulation effective with use by not habituating. In some embodiments, this technique includes the use of headphone speakers.

In some embodiments, monaural stimulation is used without headphone speakers to entrain for slow wave rhythms or beats. In some embodiments, static monaural stimulation is used, and includes a monaural acoustic waveform emitted by speakers in the device in a time-amplitude plot (horizontal—time, vertical—amplitude). Some embodiments include use of a dynamic stimuli (such as dynamic frequency) to overcome habituation processes of the brain. In some embodiments the monaural simulation is accompanied by white, pink or brown noise.

In some embodiments, the entrainment rhythms or beats (produced by binaural or monaural stimulation) are heard by a subject. In some embodiments, the entrainment rhythms or beats are generated as haptic vibrations that can be felt by the subject in addition to being heard. In some embodiments, the haptic vibrations are felt by the subject, and the subject does not hear the entrainment rhythms or beats. In some embodiments, sleep entrainment rhythms, sleep entrainment beats or haptic vibrations are produced by one or more speakers. In some embodiments, sleep entrainment rhythms, sleep entrainment beats or haptic vibrations are produced by a haptic motor.

Deep Sleep Boost™ (DSB) and Gentle Wake-Up™ (GWU) Technologies

A DSB technology or a GWU technology may include, for example, a device for respectively promoting restorative sleep or minimizing sleep inertia or fatigue upon waking. Such a device might include a brain stimulator for non-invasive stimulation of the brain at various frequencies, an alarm, and/or a sleep monitor that controls the brain stimulator and the alarm, and monitors a subject's neurophysiology. The monitor may be configured to predict brain activity indicating deep sleep slow-wave activity and/or activate the brain stimulator to emit low frequency tones. In some embodiments, at a pre-determined transition time, the monitor activates the brain stimulator to emit high frequency tones to transition the subject from deep sleep to light sleep. At a pre-determined alarm time, the sleep monitor may activate the alarm to awaken the subject. DSB or GWU may use any of the vibration sources, sound sources, or control components described herein, or may integrate user feedback as provided herein.

Figure 2:
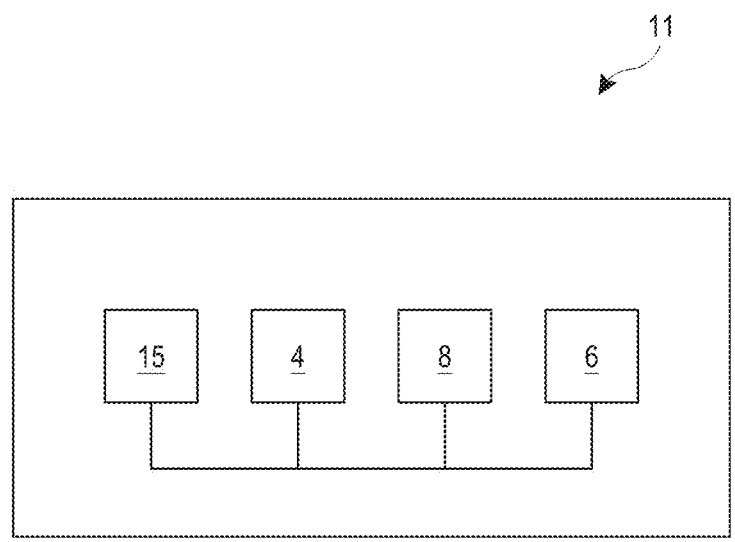
FIG. 2 is a schematic block diagram of an embodiment of a device with DSB and/or GWU technology.

FIG. 1 and FIG. 2 show illustrative embodiments of a wake-up device. FIG. 1a pillow 2 supports a device 15 for emitting tones which is in communication with a monitor 11 and an alarm 18. The alarm 18 is placed on a nightstand, and includes at least one speaker (not depicted) and a vibrator (not depicted). The device 15 can include one or more speakers (not depicted) and/or one or more vibrators (not depicted). As shown schematically in FIG. 2, the device 15 can be integrated into the monitor 11. The monitor 11 may include one or more sensors, such as an accelerometer 8, for monitoring a biosignal of the user 10, a speaker 4, a vibrator 6, and a device 15 with electronic circuitry and/or other components to predict when the user 10 is in a desired sleep state. In some embodiments the accelerator 8 is a LIS2DH IMU sensor. The monitor 11 can include a speaker 4 and a vibrator 6, either as components separate from the device, or as components integrated into the device 15. The monitor 11 and/or device 15 may or may not contact the user 10. The monitor 11 and/or device 15 may be inside the pillow on which a user's head rests. Other sensor arrangements may be used to detect one or more biosignals of the user. Examples of biosignals include body temperature, temperature gradients, blood pressure, galvanic skin response, and eye or other body movement. One or multiple sensors may be used in one or multiple locations.

Figure 3:
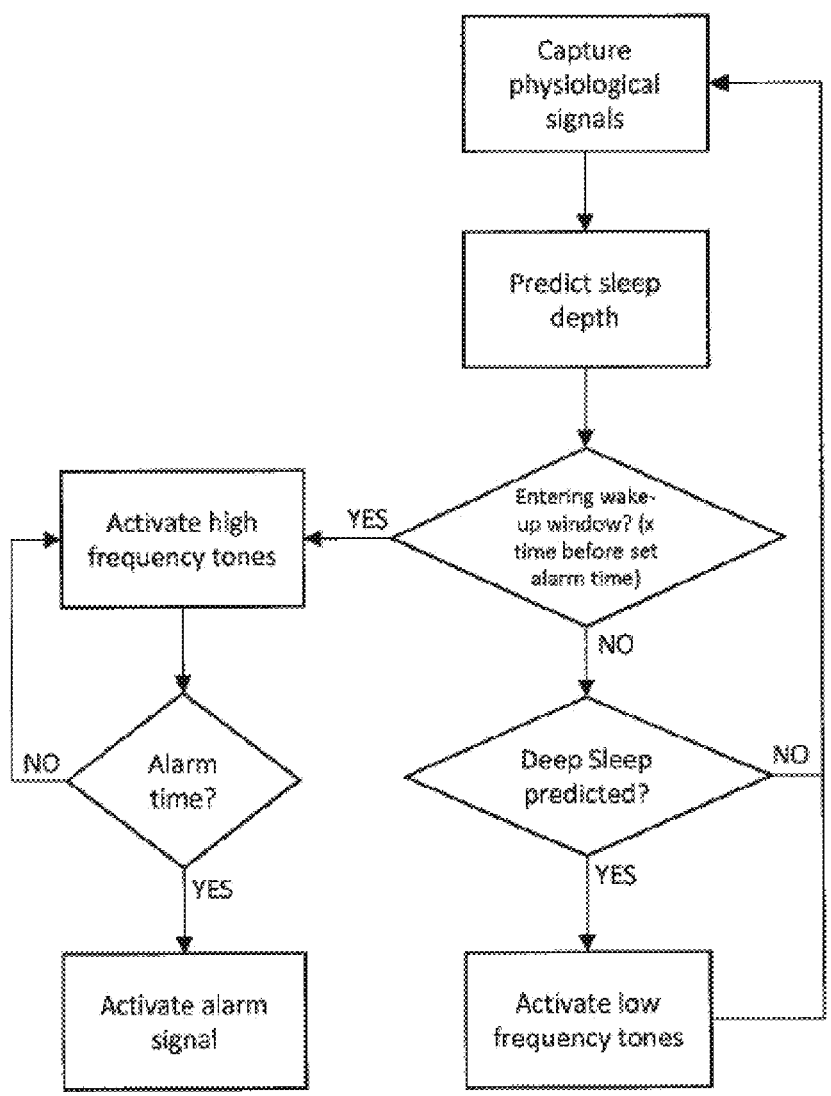
FIG. 3 is a schematic representation of a wake-up algorithm.

The device 15 may process information from the sensors (e.g., accelerometer 8) using any suitable algorithm to determine the sleep state of the user. The device 15 may predict when the user will be in a deep sleep state using, for example, the algorithm shown in FIG. 3. After receiving signals from the sensor that the user is in deep sleep, the device 15 may send an output to the speakers to emit low frequency tones that enhance deep sleep. At the set transition time, the device 15 may send an output to the speakers to emit high frequency tones (for example 8-12 Hz) that transition the user from deep sleep to light sleep. At a predetermined wake-up time, the device 15 may sound an alarm to wake the user 10. The monitor 11 and the alarm 18 may communicate in any suitable way, such as by a wired (e.g., cable, Ethernet, USB, or the like) or wireless link 16. The wireless link 16 may include any suitable communication network or networks (e.g., Bluetooth, wireless local area network, Wi-Fi, cellular network, mobile network, etc.). Based on information from the monitor 11, the alarm 18 may awaken the user 10 by any means such as by activation of a buzzer, a radio, a flashing light, haptics, scents or odors, and/or any other suitable means.

Figure 4:
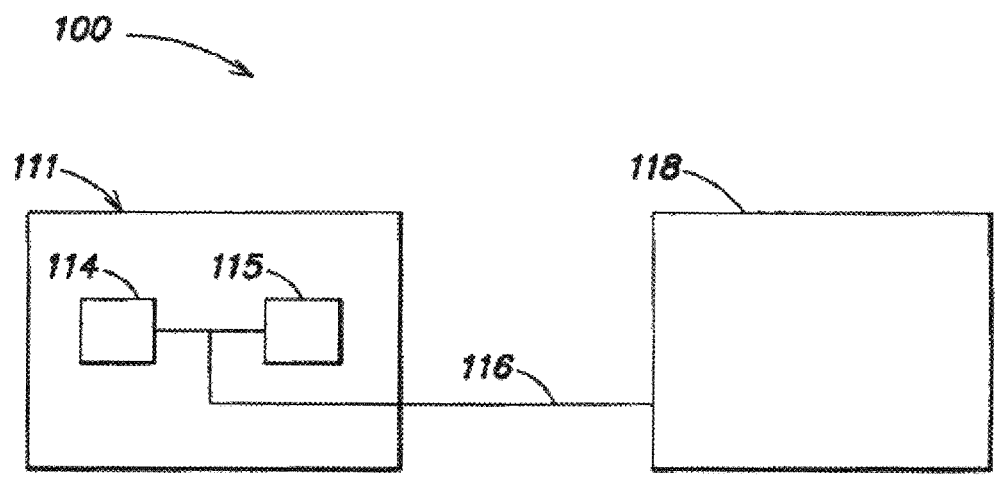
FIG. 4 is a schematic block diagram of an embodiment of a device with DSB and/or GWU technology.

As shown in FIG. 4, the monitoring portion 111 may include a predicting portion 115 to assist in determining the user's sleep state. The monitoring portion 111 or predicting portion 115 may use sensed information from the sensing portion 114, a sleep history of a user from prior sleep periods, a pre-determined hypnogram, any combination thereof or any other device or information to determine or predict the user's sleep state. The predicting portion 115 may use any suitable data or algorithm. For example, the predicting portion 115 may use the wake-up algorithm in the embodiment shown in FIG. 3. The sleep state of the user may be actively monitored and used to readjust occurrences predicted by the predicting portion 115 at any time.

Information about a user's sleep state or degree of wakefulness may be determined by the sensing portion 114. The information may also be indicated to the predicting portion 115. If the user is likely to enter the desired sleep state more than once throughout the night, the predicting portion 115 may guide the wake-up device in predicting during which occurrence of the desired sleep state the user wishes to be awakened, and a wake-up condition may then be initiated at the appropriate time by a high frequency tone that moves the user from deep sleep to light sleep. In some embodiments, the user may set a wake-up time. When the user sets a wake-up time, the high frequency tones are emitted at a predetermined time interval preceding the wake-up time set by the user. The time interval could also be determined by the user's predicted sleep stage, movement profile, or other physiological measurements.

The alarm portion 118 may perform additional functions or contain additional accoutrements. For example, the alarm portion 118 may include a speaker that projects a sound to awaken the user from sleep. An AM/FM radio, cassette, CD or MP3 player, or interface to a computer or computing device incorporating a speaker, and any appropriate controls may be included with the alarm portion 118 and/or speaker.

The alarm portion 118 may also contain a light which may be activated at desired times, as determined by the monitoring portion 111, to expose the user to light (e.g., from a lamp or from a computer or computing device incorporating a monitor capable of emitting light). Light exposure may inhibit melatonin production; therefore, a user may be more likely to awaken gracefully after being exposed to the light. In some embodiments, the alarm portion 118 is located in the pillow and uses speakers and a vibrator. The volume emitted by the speakers may be adjusted by the position of the user's head or ear. The user may also be able to manually adjust the volume. In some embodiments, the closer the user's head or ear is to the speaker, the lower the volume of noise is emitted, and the farther away, the louder the volume of noise. Sensor data can be analyzed to automatically adjust operating parameters of the alarm portion 118, so as to provide optimal performance without the need for the user to manually adjust operating parameters.

Figure 5:
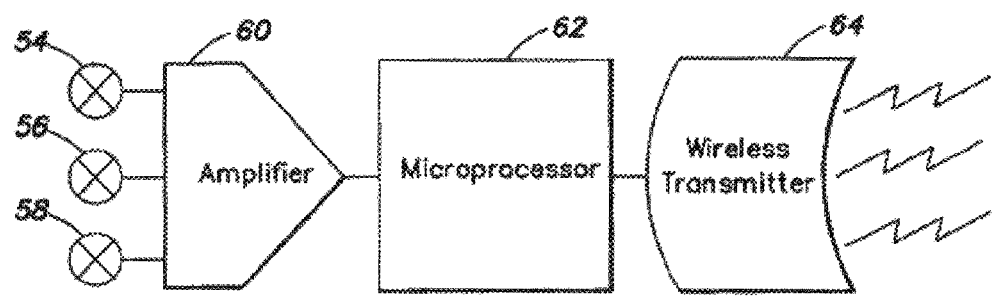
FIG. 5 is a schematic block diagram of a sensor part of a device with DSB and/or GWU technology.

As shown in the embodiment depicted in FIG. 5, the device may include sensors such as the three sensors indicated by 54, 56 and 58. Signals from these sensors 54, 56, 58 may connect to a circuit board (not shown) and may be amplified by an amplifier 60. The amplifier 60 may use a large gain to bring the differential between the signal sensors 54, 56 up to a level where it can be used as an input into an Analog to Digital Converter (ADC). The ADC may, in some embodiments, be integrated into a microprocessor 62. The amplified signals may be converted to a digital signal by the ADC, which may use a Right Leg Driver (DRL) system to eliminate common mode noise.

Figure 6:
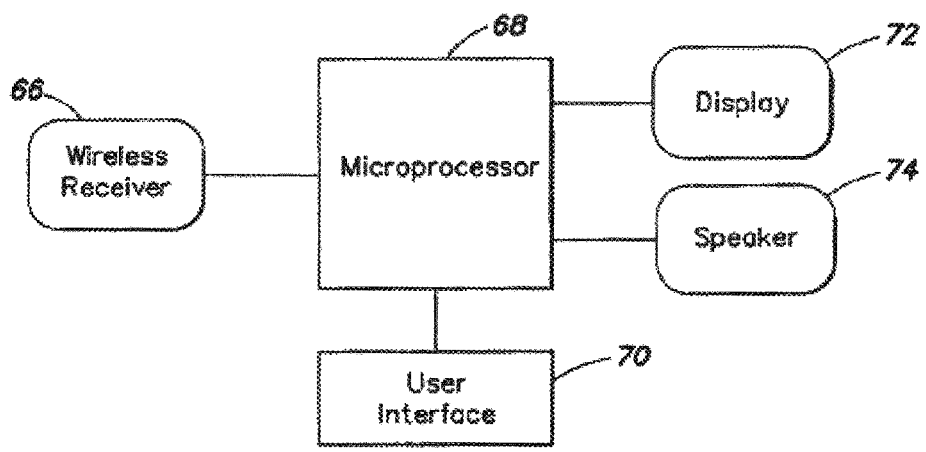
FIG. 6 is a schematic block diagram of a clock part of a device with DSB and/or GWU technology.

The digital signal may be read by a microprocessor 62 at defined signal transit times. The microprocessor 62 may determine the transmit times based on predetermined values and may wirelessly transmit the digital signal to the alarm clock unit or other device (e.g., a computer or a computing device, such as an iPhone, smartphone, or mobile device), an embodiment of which is shown in FIG. 6, using the wireless transmitter 64. The microprocessor 62 may arrange wireless transmission times to minimize power usage. In addition, the wireless transmitter may be, but need not be, integrated onto the microprocessor 62. In some embodiments, transmission is not wireless, but is along a wire.

As shown in FIG. 6, the alarm unit may include a wireless receiver 66 to communicate with a device in a pillow, for example, by using electromagnetic waves for transmission. A Digital Signal Processor (DSP) 68 on the alarm may analyze the received data from the device in the pillow according to a sleep state detection algorithm. The DSP 68 may also run a wake-up algorithm, and decide when to awaken a user. The alarm may also incorporate a memory (computer hardware integrated circuits to store information for use by a computer) to store algorithms, patient data obtained from sensors, or input data from the patient regarding sleep quality or preferences or choices for device operation. Alternatively, the alarm can be integrated into the device, and the device can contain a DSP and/or memory. In some embodiments, the device and/or alarm communicates wirelessly (e.g., via Bluetooth connection) to a computer or hand-held personal computing device (e.g., iPhone, smart phone, mobile device). By use of an app (software designed to run on smartphones and other mobile devices, or to run inside a web browser), the operation of the device can be controlled, user preferences can be input, and sensor data can be stored for later use (e.g., analysis by a health care provider such as a physician or other sleep professional to diagnose, monitor, or modify treatment of a sleep disorder) or analyzed (e.g., to optimize performance by analyzing trends, identifying correlations, etc.). The processor (e.g., DSP) and/or memory can be employed to track sleep patterns, analyze sleep cycles, and to retain sleep data, e.g., in the memory or on a cloud server. The operation of the device can be modified by the user (e.g., via the alarm, device, and/or computer or computing device) to adjust the volume and gentle wake up time.

In one embodiment, the user may choose a napping mode. In some embodiments, the user may be awakened at the end of an optimal nap time, such as 20 or 30 minutes. A nap time may be set to an amount of time that allows the user to avoid entering deep sleep. The nap time may also be an amount of time that allows the user to enter deep sleep. In addition, the user may set a wake-up time to avoid napping for too long. For example, if a user has a 4 pm appointment, the user may set a 30 minute nap time and a 3:55 pm wake-up time. In such a case, if the user lies down for a nap at 3 pm and falls asleep at 3:40 pm, the user will not oversleep because the user would be awakened at the 3:55 wake-up time instead of 30 minutes after falling asleep.

Integration

Some embodiments of the systems, methods, and devices provided herein relate to a vibration source integrated with a sound source. In some embodiments, the vibration source and the sound source are included as part of the same physical system or device. For example, in some embodiments a pillow or pillow insert (or other insert) includes both a vibration source and a sound source. In some embodiments, the vibration source and the sound source are included as part of the same physical device within a pillow, bedding item, or other structure as described elsewhere herein. In some embodiments, the vibration source and the sound source are included as part of the separate devices, but are both included within the same pillow or bedding item.

In some embodiments, the vibration source and the sound source are included as part of separate but integrated systems or devices. For example, in some embodiments a pillow or pillow insert (or other insert) includes a vibration source a sound source. In some embodiments, the vibration source is inserted into or placed next to a pillow, while the sound source is part of a separate speaker component that plays a sound while the vibration device produces a vibration. For example, the sound source may be a phone or cellphone speaker, or a radio speaker that is integrated with the vibration device. In some embodiments, the separate vibration source and sound source are connected electronically by, for example, a wire or cord. In some embodiments, the separate vibration source and sound source are connected wirelessly.

Some embodiments include another device or component, or another sleep aid device or component. For example, some embodiments include Deep Sleep Boost™ (DSB) and/or Gentle Wake-up™ (GWU) technology. Some embodiments include a light dimmer or scent emitter. Some embodiments utilize one or more components of DSB and/or GWU. Some embodiments include a processor, a battery, an accelerometer, a memory, and/or a communication component. In some embodiments, the communication component includes a Bluetooth, Wi-Fi, infra-red, and/or network connection. In some embodiments, the communication component communicates with a processor, computer, phone, cellphone, smartphone, television, stereo, or other device.

Some embodiments include arrays of scent nodes that release compounds contained in lavender oil, vetiver oil, vanillin, or other pleasant odors. Some embodiments include unpleasant odors such as a sulfurous or acidic odor to induce waking. Some embodiments do not interface the nasal region directly but can still deliver nasal stimulation to enhance sleep and/or relaxation.

Some embodiments include a monitoring portion which includes a predicting portion that assists in determining the sleep state of the user and may use sensed information from a sensing portion, a sleep history of a user from prior sleep periods, a pre-determined hypnogram, any combination thereof or another device or information. In some embodiments, the predicting portion uses any suitable data or algorithms, such as a wake-up algorithm. In some embodiments, the sleep state of the user is actively monitored and this information is used in actively readjusting any predicted occurrences.

Some embodiments include an alarm portion, which may also perform additional functions and contain additional accoutrements. Some embodiments include an AM/FM radio, cassette, CD and/or MP3 player. Some embodiments include a light which may be activated at desired times, as determined by monitoring the portion, to expose the user to light. In some embodiments, light exposure inhibits melatonin production; therefore, a user may be more likely to awaken gracefully after being exposed to light.

Some embodiments include arrays of lights emitting diodes to provide photic stimulation. In some embodiments, the photic stimulation changes over time its composition of frequency of light (i.e. color) or amplitude (i.e. luminosity).

In some embodiments, the user may choose a napping mode. In some embodiments, the user may be awakened at the end of an optimal nap time, such as 20 minutes. The optimal nap time may be set so that the user may avoid entering deep sleep; however, other times may be used. In addition, the user may set a wake-up time, so that the user may not have to worry about not being awakened by an appropriate time. For example, if a user has a 4 p.m. appointment and lies down for a nap at 3 p.m. but does not actually fall asleep until 3:30 p.m. the user may set a wake-up time of 3:55 p.m. so that the user will not oversleep.

In some embodiments, gyroscopes are used to capture motion data indicative of movement. In some embodiments, thin force sensors are used to capture motion data indicative of movement. In some embodiments, pressure sensors are used to capture motion data indicative of movement. In some embodiments, data provided by the gyroscopes, thin force sensors, or pressure data are processed and used to predict sleep depth or determine an appropriate vibration and/or sound setting. Some embodiments include one or more contactless sensors such as a microphone, camera, laser, which capture sound and/or motion data of the user. For example, a microphone may capture breathing sounds of the user, or a camera may capture chest motion data that relates to the user's breathing. A processor or other device may determine the user's sleep state via the breathing sounds or chest motion data.

In some embodiments, rhythmic or constant stimulation, such as repetitive droning or a flat pink noise stimulation, is used to promote synchronization in brainwave activity via the frequency-following response. In some embodiments, to promote a state of wakefulness, intermittent stimulation in irregular intervals can serve to desynchronize brainwave activity. In some embodiments, use any combination of non-invasive methods of stimulation through the pillow topper to promote waking or various states of sleep by use of intermittent or rhythmic stimulation, respectively.

In some embodiments, an array of one accelerometer is at the center of the pillow topper along with a vibrating motor, and two speakers on opposite corners. In some embodiments the placement of the speakers is optimal for delivery of acoustical stimulation in a balanced manner, while minimizing the possibility of overstimulation where the user is sleeping on her side and her ears are directly over the speakers.

In some embodiments, the accelerometer data is processed into magnitude data and extracted into features that are representative of different types and intensities of physiologically significant movements. In some embodiments, the processing is done locally in a pillow topper or insert. In some embodiments, the processing is transmitted wirelessly to a portable device such as a mobile phone, where the processing occurs remotely and stimulation parameters are transmitted back to the pillow topper or insert.

In some embodiments, speakers are stereo and alternate in volume for vestibular stimulation. For purposes of illustration and not limitation, vestibular stimulation can be delivered with a rocking bed that moves the whole body, or through stereo headphones that manipulate the sources of sound more precisely than otherwise.

Some embodiments include a sleep tracking and waking optimization system, which includes one or more of a bio-amplifier, a processing control unit, and an alerting module. In some embodiments, the bio-amplifier includes one or more of an EEG/pressure sensor matrix, and a raw signal processor.

Some embodiments include a plurality of accelerometers. In some embodiments, the plurality of accelerometers includes 1, 2, 3, 4, 5, 6, 7, 8, 9, 10, 11, 12, 13, 14, 15, 16, 17, 18, 19, or 20 accelerometers, or any number therebetween. In some embodiments, the plurality of accelerometers includes accelerometers arranged in a 2×2 matrix layout in relation to each other. In some embodiments, the plurality of accelerometers includes accelerometers arranged in a 2×1, 2×2, 1×3, 3×2, 3×3, 4×1, 4×2, 4×3, 4×4, 5×1, 5×2, 5×3, 5×4, or 5×5 matrix layout in relation to each other. In some embodiments, the plurality of accelerometers includes accelerometers is arranged in a non-matrix layout. In some embodiments, the accelerometers include at least one accelerometer that measures a user's respiration rate. In some embodiments, the accelerometers include at least one accelerometer that measures a user's heart rate.

In some embodiments, the plurality of accelerometers arranged in a matrix layout includes accelerometers arranged in a square or rectangle formation. For example, accelerometers in a 2×2 matrix layout may be arranged in a square formation. Since individual accelerometers may inherently have some amount of noise present in their measurements, a benefit of using a 2×2 array is that it may allow for a high degree of noise cancellation that greatly increases the accuracy of the combined measurement compared to a single measurement or a single accelerometer.

In some embodiments, the accelerometer or plurality of accelerometers is positioned next to, under, on top of, or integrated into the same device as a vibration source and/or sound source. In some embodiments, the accelerometer or plurality of accelerometers is positioned next to, under, on top of, or integrated into a pillow. For example, a single accelerometer lies on top of a pillow or is held in place by one or more straps on top of a pillow. In some embodiments, a plurality of accelerometers lies underneath a pillow or is held in place by one or more straps underneath a pillow. In some embodiments, the plurality of accelerometers underneath the pillow includes four accelerometers in a 2×2 matrix. In some embodiments, one or more accelerometers are included in a wearable device such as a wrist band or headband that communicates wirelessly or electronically with a processor.

In some embodiments, a processor or other device uses the plurality of accelerometers or other sensors to detect a sleep state of a subject. For example, a plurality of accelerometers arranged in a 2×2 matrix may detect a subject's sleep state. Examples of sleep states include, but are not limited to, awake, REM sleep and non-REM sleep. Non-REM sleep may include light sleep and deep sleep.

In some embodiments, a subject's REM sleep and non-REM sleep states alternate within a sleep cycle. A sleep cycle may be, for example, about 90 minutes. As sleep cycles continue throughout a normal night, each successive sleep cycle may shift towards a higher proportion of REM sleep. The transition to REM sleep may coincide with physical changes such as electrical bursts originating in the brain stem, and fluctuations in respiration, thermoregulation, circulation, and muscle tone. In some instances, these physical changes or fluctuations do not occur in other sleep states or when the subject is awake. The plurality of accelerometers or other sensors may detect these changes. For example, a plurality of accelerometers or other sensors may detect fluctuations in the subject's respiration, thermoregulation, and circulation. In some embodiments, the detection of these or other changes allows for the determination of the subject's sleep state.

In some embodiments, a plurality of accelerometers arranged in a 2×2 matrix differentiates or enables differentiating whether a subject is awake or in REM sleep. For example, the 2×2 matrix of accelerometers may detect the subject's heart rate, breathing, and movement, to determine whether the subject is awake or in REM sleep. The plurality of accelerometers may determine that the subject is not awake, or not in REM sleep, or that the subject is awake or in REM sleep. Other matrix arrangements of accelerometers, such as those described above, or one or more other sensors, may also differentiate or enable differentiating whether a subject is awake or in REM sleep. In some embodiments, a single accelerometer, a plurality of accelerometers, or one or more other sensors, differentiates or can enable differentiating whether a subject is in REM sleep, light sleep or deep sleep.

Some embodiments include artificial intelligence or unsupervised learning. In some embodiments, supervised learning is used to train the AI algorithm. In some embodiments, the artificial intelligence or unsupervised learning identifies a subject's sleep patterns. The identified sleep patterns may then be used modify or enhance the subject's sleep by any of the methods described herein, such as by the generation of white, pink or brown noise or vibrations that stimulate the subject's vagus nerve. In some embodiments, the artificial intelligence or unsupervised learning generates information about feedback loops relating a subject's sleep. For example, a certain amount of white, pink or brown noise or other stimulation may be needed to enhance a subject's transition from being awake to deep sleep, or from REM sleep to deep sleep. The artificial intelligence or unsupervised learning may determine what level or type of stimulation is necessary, and the stimulation may be adjusted accordingly in future sleep cycles. The artificial intelligence or unsupervised learning may also identify a subject's optimal duration of time for each sleep state within a sleep cycle, or identify an optimal number or frequency of sleep cycles within a night or sleep period, and adjust the stimulation to achieve the optimal duration of a sleep state, or number or frequency of sleep cycles.

Control

Some embodiments of the systems, methods, and devices provided herein include an input and/or control component that provides input and/or control over the vibration source and/or sound source. In some embodiments, the input and/or control component is accessed by a user or person who controls the vibration source and/or sound source through the input and/or control component.

In some embodiments, the vibration source and/or the sound source are controlled directly by at least one control mechanism such as, but not limited to, a button, a knob, a dial, a slider, and/or any other control mechanism. In some embodiments, the control mechanism is included in a remote-control device. In some embodiments, the control mechanism is physically attached to the vibration source and/or the sound source.

In some embodiments, a computer program or application (such as an app on a cellphone or other smart device such as a smart television) connects with the vibration source and/or the sound source. In some embodiments, the connection is electronic, and includes, but is not limited to, a wire or a cord. In some embodiments, the connection is wireless. In some embodiments, program or application provides a graphical or visual interface for control of the vibration source and/or the sound source. In some embodiments, the program or application is included in a device that communicates with the communication component described above.

In some embodiments, the input and/or control component modifies or changes the sound or vibration. In some embodiments, the input and/or control component modifies the vibration's speed, strength, repetition, and/or pattern. In some embodiments, the input and/or control component changes the vibration into a different type of vibration.

In some embodiments, the input and/or control component modifies the sound's pitch, frequency, period, loudness, volume, amplitude, intensity, timbre, tone, speed, strength, repetition, and/or pattern. In some embodiments, the input and/or control component changes the sound to a new sound, such as for example to a new sound or to a new white, pink or brown noise.

In some embodiments, the input and/or control is provided by the user's fingertips. In some devices, the input is provided by the user's voice and/or physical actions. In some embodiments, the vibration source and/or sound source are controlled by a timer.

Some embodiments include a termination sequence and/or initiation sequence. For example, the sound and/or vibrations may initiate or end with a tapered volume or intensity. In some embodiments, the termination sequence and/or initiation sequence are controlled by a predetermined timer that is built into the device or added via user input. In some embodiments, the termination sequence and/or initiation sequence are controlled by a physiological condition of the subject using the device, such as the subject's movement, heart rate, and/or respiration rate. In some embodiments, the sound and/or vibrations are initiated when the subject is awake and/or lies down. In some embodiments, the sound and/or vibrations are terminated when the subject is asleep and/or gets up.

Some embodiments include mechanical sensors used singularly or as an array of accelerometers, ranging from one to sixteen. In some embodiments, the array of accelerometers captures motion data indicative of movement. In some embodiments, the data is processed to determine whether the captured motion is physiological (hypnic jerk), environmental (pets jumping on a bed), and the origin of the motion is (for example, a head twitch versus a leg jerk) to predict sleep depth and to determine an appropriate sound and/or vibration setting.

In some embodiments, use of mechanical sensors to capture physiological data is low-fidelity but adequate for use of predicting sleep depth or determining the appropriate sound and/or vibration setting. For purposes of illustration and not limitation, a number of features can be extracted from the motion captured from one accelerometer that are indicative of sleep depth, such as magnitude or standard deviation. These features can be processed using algorithms that use machine to classify the user's state of sleep.

In some embodiments, an increased number of mechanical sensors in an array can capture finer movements and be used to extract additional features such as heart rate and respiratory, where the force displacements require more sensitive motion capturing.

In some embodiments, the stimulation used by the device are further optimized to determine the best intensity or location of stimulation. For instance, if the user is lying on her side, and there are two or more speakers, acoustical stimulation in one speaker may be louder than in another, compared to if she's lying on her back, where the speakers would then in some embodiments have a balanced acoustical output.

In some embodiments, mechanical sensors are used to determine the pillow type that the user has installed the device onto or into. In some embodiments, a calibration step where the user puts her head down onto the device and pillow will enable the mechanical sensors to capture motion data that differs based on the type of the pillow. For instance, a softer down pillow is compressed at a constant, faster rate than a memory foam pillow, which is compressed more rapidly at first and then at a slower rate following initial distribution of force.

Some embodiments, through accelerometer readings of head and torso motion, predict whether the user is awake, in light sleep, in REM sleep, or in deep sleep. In some embodiments, when the device determines the user is in deep sleep, the device selects a different sound and/or vibration setting than when the device determines the user is in light sleep or awake.

In some embodiments, the volume emitted by the speakers may be adjusted by the position of the user's head. In some embodiments, the closer to the speaker, the lower the volume of noise emitted, and the farther away, the louder the volume of noise.

Inducing Sleep or Relaxation

Some embodiments of the systems, methods, and devices provided herein relate to inducing sleep and/or relaxation. In some embodiments, the vibrations from the vibration source induce sleep and/or relaxation in a subject. In some embodiments, the sound from the sound source induce sleep and/or relaxation in a subject. In some embodiments, a combination of the vibrations from the vibration source, and the sound from the sound source, induce sleep and/or relaxation in a subject. In some embodiments, the subject feels refreshed after using the system, device, or method.

User Feedback

A difficulty in some embodiments is that DSB may be hard to optimize. For example, some people may move around more during sleep than an average person, and some people may move around less during sleep than an average person. This may make it difficult to determine a sleep stage using movement data alone. In such examples, if a general movement threshold based on an average user is used to determine a sleep stage, the person who moves around more than average may incorrectly be characterized as awake or in a light sleep stage when the person is actually in a deep sleep stage, and the person who moves around less than average may incorrectly be characterized as in deep sleep when the person is in a light sleep stage. In such a case, the DSB may be activated more often or less often than is necessary in order to improve sleep.

Figure 13:
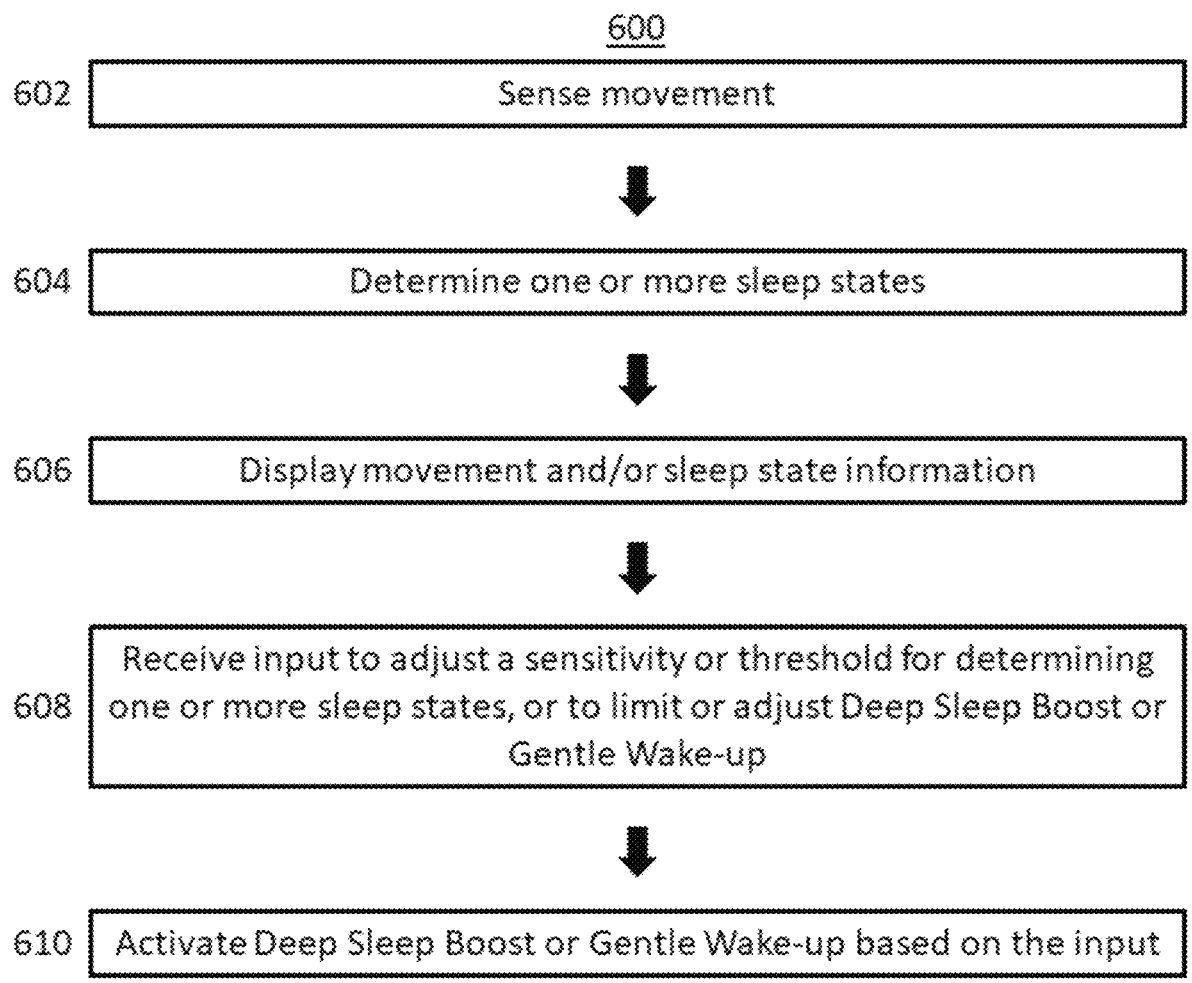
FIG. 13 depicts a method of providing DSB and/or GWU to a subject.

To solve this problem, some embodiments of the methods, systems and devices provided herein integrate user feedback. For instance, as shown in the flowchart of FIG. 13, some embodiments include a method for providing Deep Sleep Boost™ (DSB) to a subject 600. Some embodiments display movement and sleep state information to a subject after a device or system as described herein senses movement and identifies sleep states of the subject during a sleep period. For example, the subject may go to bed on a pillow with a 2×2 array of accelerometers that sense movement of the subject during sleep, and transmit movement data to her phone or to another device that transmits the movement data to the phone. When the subject wakes up, a program or application on the phone or other device receives input from the user to adjust the movement threshold used to determine that the user is in any given sleep state, or input that limits or adjusts the amount of DSB or GWU the user receives the next time he or she sleeps.

Some embodiments of the methods, devices, and systems described herein include sensing movement 602. For example, some embodiments include sensing movement of a subject during a first sleep period. The sensing may be performed by, for example, an accelerometer. The first sleep period may be less than an hour, or may last 1, 2, 3, 4, 5, 6, 7, 8, 9, 10, 11, 12, 13, 14, or more hours, and may be during the day and/or at night. For example, the first sleep period may be the first night the subject uses the method, device or system described herein. The first sleep period may also be another night after the first night the subject uses the method, device or system.

Some embodiments include determining one or more sleep states 604. For example, some embodiments include determining multiple sleep states of the subject throughout the first sleep period. In some embodiments, said determining is based on the sensed movement of the subject, and/or on at least one predetermined threshold amount of movement. For example, a predetermined threshold may be set, based on an average subject, for a transition between each sleep state. In some embodiments, a decrease in movement below the threshold indicates that the subject has transitioned from light sleep to deep sleep. An amount of movement at the same or a different threshold may be used to indicate that the subject has transitioned from deep sleep to light sleep. Other thresholds may be used to indicate a transition from REM sleep to light sleep or vice versa, or from awake to REM sleep or vice versa, or any other transition between estimated sleep stages during sleep. Examples of movement data that may indicate a sleep state or a transition between sleep states include number of movements per second or per minute, or an amount or frequency of abrupt or fast movements (as opposed to slow movements). Any of these thresholds may be pre-selected, or may be modified by a user.

Some embodiments include displaying movement and/or sleep state information 606. For example, some embodiments include displaying information about the subject's movement sensed during the first sleep period, and/or information about the sleep states determined during the first sleep period. Examples of information about the subject's movement sensed during the first sleep period include number of movements, number of movements over time, frequency of movements, abruptness of movements, and any other indicator of activity. Examples of information about the determined sleep state include awake, REM sleep, light sleep and deep sleep. The information about the subject's movement may be displayed graphically and/or via words and numbers. For example, a display may show a histogram where an x-axis includes time increments (such as 1, 2, 3, 4, 5, 6 7, 8, 9 or 10 minute increments), and a y-axis includes numbers or frequencies of movements during each time increment. Alternatively, a display may show a histogram where the x-axis includes time increments, and the y-axis includes a depiction of the subject's determined sleep state at each time increment (like, for example, the depiction in FIG. 12). In some embodiments, the display shows an overlay of sleep state information and movement information together, for example in the same histogram with a single x-axis for time, and two y-axes where sleep state is shown with one line and by one y-axis, and where movement data is shown by a second line and by a second y-axis within the same histogram as the first line and y-axis.

Some embodiments include receiving input to adjust a sensitivity or threshold for determining one or more sleep states, or to limit or adjust DSB or GWU 608. For example, some embodiments include obtaining input from the subject. In some embodiments, the input is used to increase or decrease the at least one threshold amount of movement for determining sleep states. Some embodiments include setting a second threshold amount of movement. Some embodiments include obtaining input by providing a display to a subject to input whether the subject is considered a light sleeper, a deep sleeper, or an average or normal sleeper, or about whether the subject moves around a lot, more than average, less than average, only a little, or an average amount during sleep. Some embodiments include obtaining input from the subject to increase or decrease a predetermined threshold amount of movement to set a second threshold amount of movement. The second threshold may be used in a second sleep period. Any method of obtaining input known in the art may be used. For example, the subject or another user may provide input through a graphical user interface or by voice command. The threshold may be increased for a "light sleeper" that moves a lot during sleep, for example, by increasing the number or frequency of movements that would indicate the subject to be transitioning between a sleep state, such as from light sleep to deep sleep, or the threshold may be decreased for a "deep sleeper" that moves less during sleep. By allowing a user to change the threshold, a problem of having DSB be activated too much or too little may be solved for future sleep periods. Some embodiments include activating DSB or GWU based on the input 610.

In some embodiments, the subject is considered a "deep sleeper," or is considered to move around only a little, when the subject moves less frequently during a sleep period or during a sleep stage than an average subject. For example, a subject considered a "deep sleeper" may move 10%, 20%, 30%, 40%, 50%, 60%, 70%, 80%, 90%, 100%, 200%, 300%, 400%, 500%, 600%, 700%, 800%, 900%, or 1000% less frequently than an average subject.

In some embodiments, the subject is considered a "light sleeper," or is considered to move around a lot, when the subject moves more frequently during a sleep period or during a sleep stage than an average subject. For example, a subject considered a "light sleeper" may move 10%, 20%, 30%, 40%, 50%, 60%, 70%, 80%, 90%, 100%, 200%, 300%, 400%, 500%, 600%, 700%, 800%, 900%, or 1000% more frequently than an average subject.

In some embodiments, step 608 includes asking or prompting a subject, via an output device such as a display or speaker, to input whether the subject would like more or less DSB and/or GWU. For example, a screen may display a question about whether the subject would like to receive more Deep Sleep Boost next time he or she sleeps, and the subject may indicate "yes" or "no." In some embodiments, step 606 is optional. For example, some embodiments include receiving input 608 without displaying movement and/or sleep state information 606.

Figure 14:
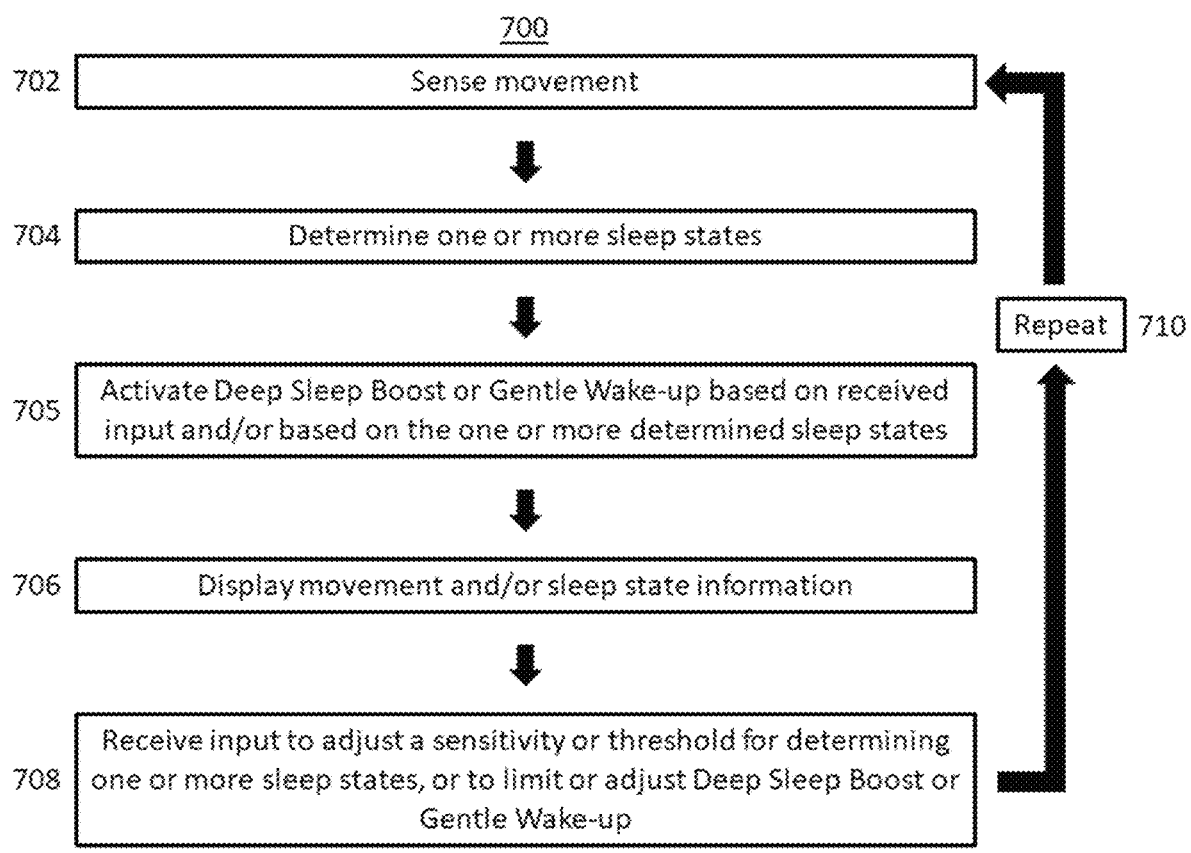
FIG. 14 depicts a method of providing DSB and/or GWU to a subject.

As one shown in the flowchart of FIG. 14, one aspect includes a method 700 that includes a feedback loop 710. Some embodiments include sensing movement 702. Some embodiments include determining one or more sleep states 704. Some embodiments include activating DSB or GWU based on received input and/or based on the one or more determined sleep states 705. In some embodiments, said sensing movement 702, determining one or more sleep states 704, and activating DSB and/or GWU based on received input and/or based on the one or more determined sleep states are performed during a first sleep period of a subject. Some embodiments include displaying movement and/or sleep state information 706. Some embodiments include receiving input to adjust a sensitivity or threshold for determining one or more sleep states, or to limit or adjust DSB or GWU 708. Some embodiments include repeating 710 any of steps 702, 704, 705, 706 and 708 one or more times. In some embodiments, said repeating 710 is optional. In some embodiments, steps 702, 704 and 705 are repeated in a second sleep period. In some embodiments, the first time step 705 is performed, the step includes activating DSB and/or GWU based on the one or more determined sleep states, but not based on received input. In some embodiments, the second or later time step 705 is performed, the step includes activating DSB and/or GWU based on received input from step 708, and based on the one or more determined sleep states. In some embodiments, the method includes a step of receiving input to adjust a sensitivity or threshold for determining one or more sleep states, or to limit or adjust DSB or GWU prior to step 702, and the first time step 705 is performed, the step includes activating DSB and/or GWU based on the received input, and not based on the one or more determined sleep states. Each step of the method described in relation to FIG. 14 may be performed by any of the methods, systems, or devices described herein, for example, as described in relation to FIG. 13.

Some embodiments include obtaining input from a user or subject before a sleep period in which the user uses the device, or without a sleep period. For example, some embodiments include a method for providing DSB to a subject. The method may include obtaining input from a subject, through a device, about whether the subject is considered a "light sleeper," a "deep sleeper," or an "average" or "normal" sleeper, or about whether the subject moves around more than average, less than average, or an average amount during sleep. The method may include determining, based on the obtained input, a threshold amount of movement for determining a sleep state of the subject. The method may include sensing movement of a subject during a sleep period. The method may include determining, based on both the sensed movement of the subject and the determined threshold amount of movement, a sleep state of the subject throughout the sleep period. The method may include activating DSB during the sleep period based on the determined sleep state. In some embodiments, determining a threshold amount of movement for determining a sleep state of the subject includes adjusting a predetermined threshold based on the obtained input.

Some embodiments include a predetermined threshold. The predetermined threshold may be, for example, factory or default settings. The factory or default settings may be based on an average or normal subject, such as a subject that moves around an average amount during sleep. The predetermined threshold may also be adjusted or initially based on user input.

In some embodiments, the problem is solved by obtaining input from the user to limit DSB or GWU during a second sleep period. For example, some embodiments include receiving input to set a limit on the amount of time that DSB or GWU is activated during the second sleep period. Some embodiments include limiting the amount of stimulation (such as sound or vibration) that the user receives during DSB or GWU. Some embodiments include limiting the amount of times DSB (or stimulation such as sound or vibration) is activated during a sleep period.

EXAMPLES

Some aspects of the embodiments discussed above are disclosed in further detail in the following example or examples, which are not in any way intended to limit the scope of the present disclosure. Those in the art will appreciate that many other embodiments also fall within the scope of the disclosure, as it is described herein above and in the claims.

Figure 7:
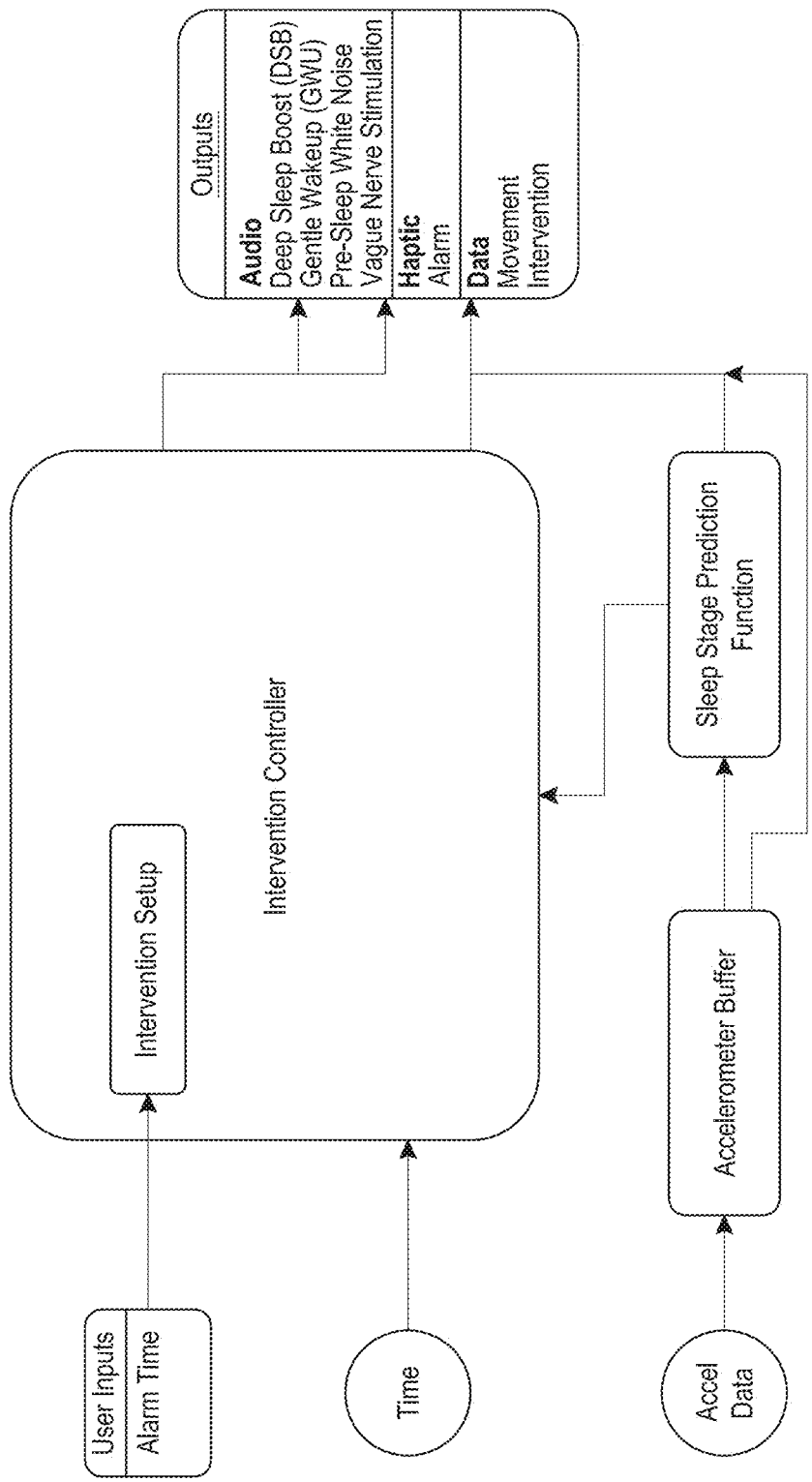
FIG. 7 is a block diagram depicting how various components are integrated in some embodiments.

Some embodiments incorporate one or more of the various elements or components described above. For example, FIG. 7 depicts how various components are integrated in some embodiments. In some embodiments, a user inputs data or information such as an alarm time. In some embodiments, the user inputted data or information is then used in an intervention step that changes or modifies a person's sleep pattern, or incorporated into an intervention setup. In some embodiments, the intervention setup is part of an intervention controller. In some embodiments, the intervention controller is influenced by one or more of various factors including time. In some embodiments, data provided by an accelerometer is processed through an accelerometer buffer. In some embodiments, the data from the accelerometer or accelerometer buffer is incorporated into a sleep stage prediction function. In some embodiments, the sleep stage prediction function is processed by or affects an intervention controller. In some embodiments, the acceleration data, acceleration buffer, sleep stage prediction function, and/or intervention controller are used to generate one or more output such as an audio, a haptic output, or a data output. In some embodiments, the audio output includes deep sleep boost technology, gentle wakeup technology, white, pink or brown noise (including pre-sleep white, pink or brown noise and/or white, pink or brown noise during sleep), and/or vagus nerve stimulation (such as the stimulation provided by a vibration source described above). In some embodiments, the haptic output includes an alarm component. In some embodiments, the data output includes movement data or intervention data. In some embodiments, one or more of these various components are integrated to provide a subject with better or improved sleep.

Figure 8A:
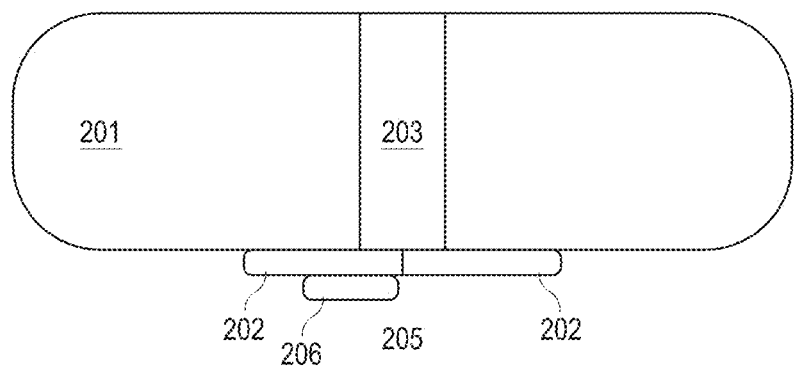
FIG. 8A shows a side view of a pillow with a vibration motor and a plurality of accelerometers strapped to the pillow.
Figure 8B:
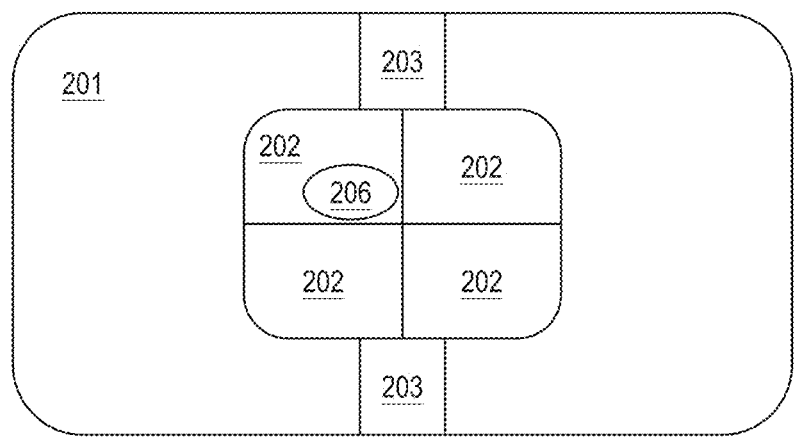
FIG. 8B shows a bottom view of a pillow with a vibration motor and a plurality of accelerometers strapped to the pillow.

Another example is depicted in FIG. 8A and FIG. 8B. FIG. 8A illustrates a side view of a pillow 201. A vibration motor 206 and a plurality of accelerometers 202 are attached to the pillow by a strap 203. A first side 204 and a second side 205 are shown. A person rests her head against the first side 204 with her neck substantially parallel to the strap 203. FIG. 8B shows the pillow 201, vibration motor 206, and plurality of accelerometers 202 attached to the pillow, as seen from a view looking down at the second side 205. The plurality of accelerometers 202 is in a 2×2 matrix formation. In the embodiment shown in these figures, the strap 203 bisects, or wraps around, the center of the pillow 201 vertically.

Figure 9A:
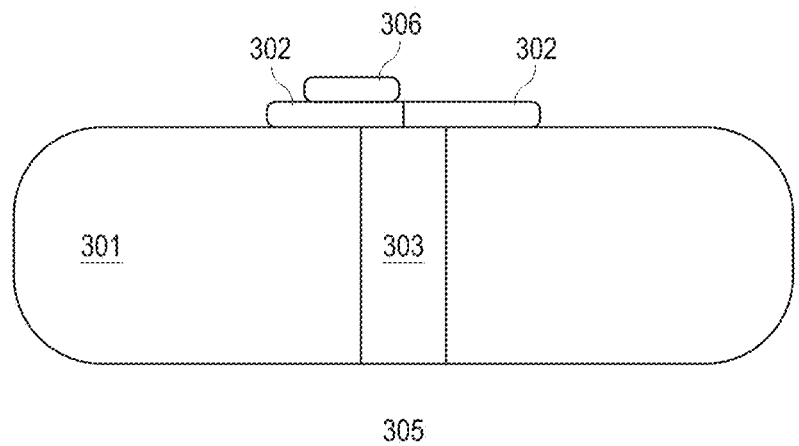
FIG. 9A shows a side view of a pillow with a vibration motor and an accelerometer strapped to the pillow.
Figure 9B:
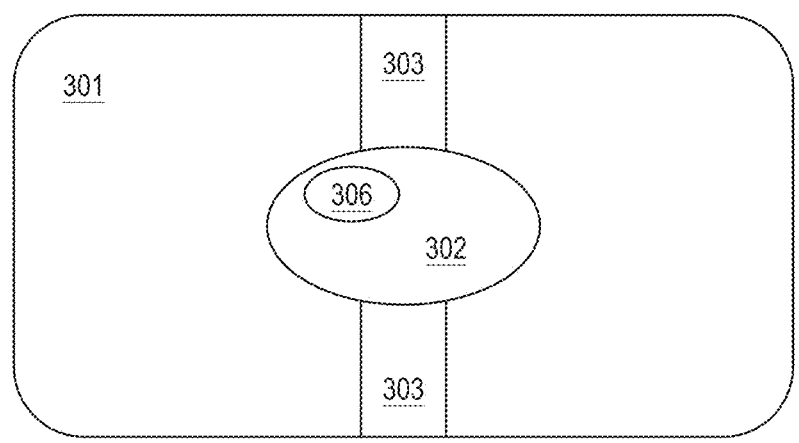
FIG. 9B shows a bottom view of a pillow with a vibration motor and an accelerometer strapped to the pillow.

Another example is depicted in FIG. 9A and FIG. 9B. A pillow 301 is shown as seen from the side in FIG. 9A. A vibration motor 306 and a single accelerometer 302 are attached to the pillow by a strap 303. A first side 304 and a second side 305 are shown. A person rests her head against the first side 304 with her neck substantially parallel to the strap 303. FIG. 9B shows the same pillow 301, vibration motor 306, and accelerometer 302 attached to the pillow, as seen from a view looking down at the first side 304. In the embodiment shown in these figures, the strap 303 bisects, or wraps around, the center of the pillow 301 vertically.

Figure 10:
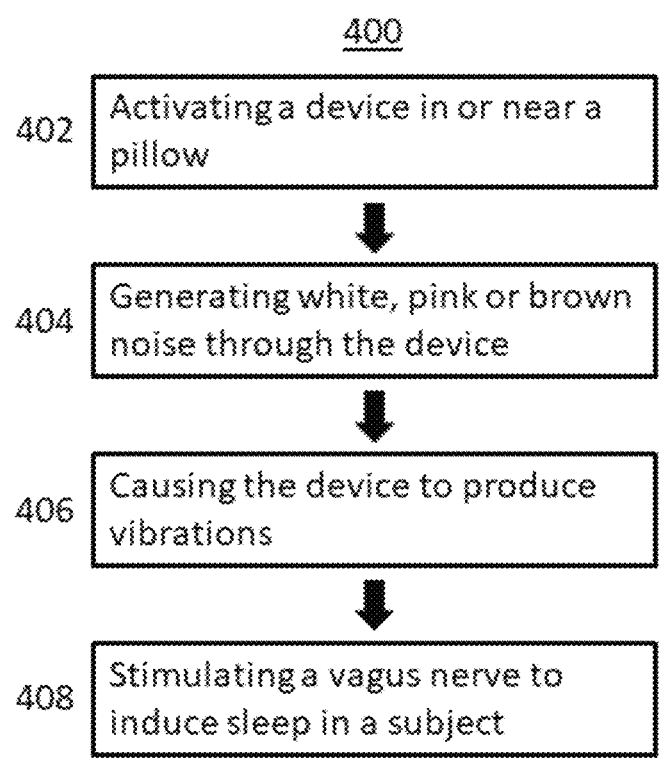
FIG. 10 depicts a method of inducing sleep in a subject.

Another example is depicted in FIG. 10, and is a method for inducing sleep in a subject 400. The method includes activating a device in or near a pillow 402, generating white, pink or brown noise through the device 404, causing the device to produce vibrations 406, and stimulating a vagus nerve to induce sleep in a subject. Stimulating the subject's vagus nerve may decrease the subject's heart rate or respiration rate 408.

Figure 11:
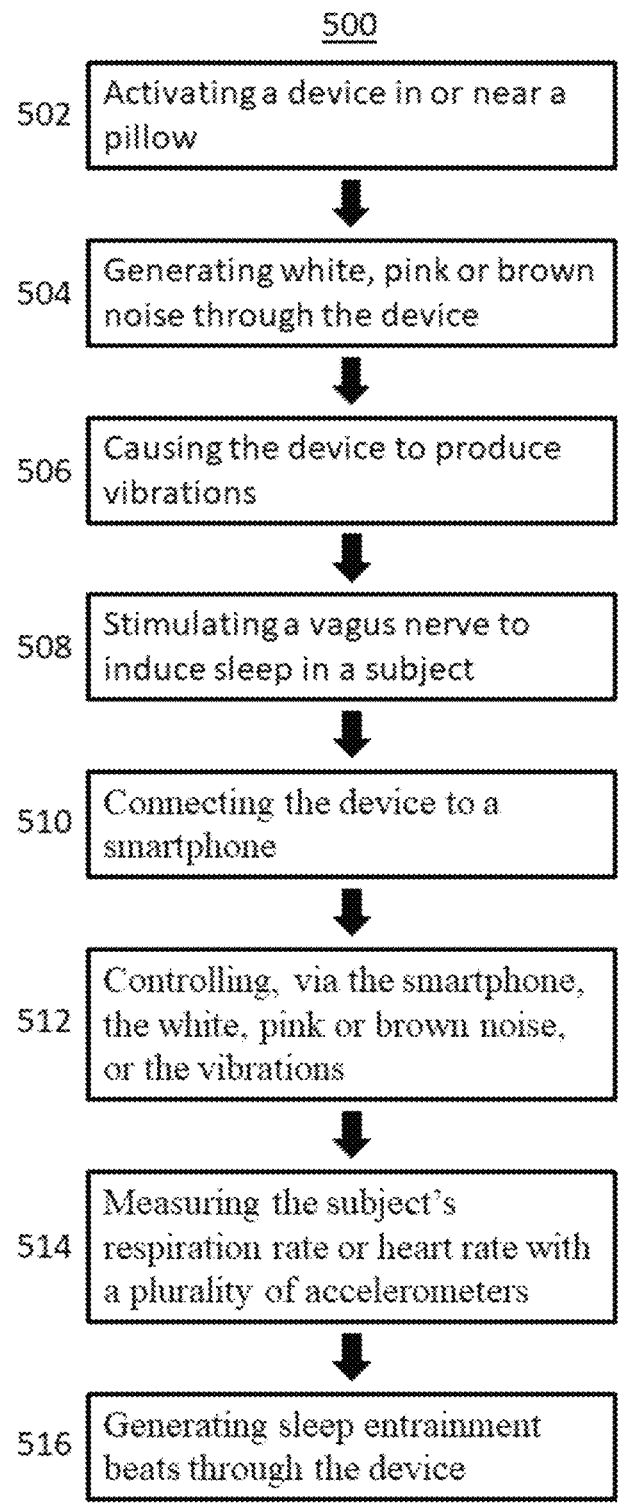
FIG. 11 depicts a method of inducing sleep in a subject.

Another example of a method for inducing sleep in a subject 500 is depicted in FIG. 11, and includes some of the same steps, all of the same steps, or similar steps as the method depicted in FIG. 10, such as activating a device in or near a pillow 502, generating white, pink or brown noise through the device 504, causing the device to produce vibrations 506, and stimulating a vagus nerve to induce sleep in a subject. Stimulating the subject's vagus nerve may decrease the subject's heart rate or respiration rate 508. The example in FIG. 11 includes the following steps: connecting the device to a smartphone 510, controlling, via the smartphone, the white, pink or brown noise, or the vibrations 512, measuring the subject's respiration rate or heart rate with a plurality of accelerometers 514, and generating sleep entrainment beats through the device 516. The connection of the device to a smartphone may be wireless. Controlling the vibrations may include controlling the speed, strength, rhythm, repetition, or pattern of the vibrations. Controlling the white, pink or brown noise may include controlling the pitch, frequency, period, loudness, volume, amplitude, intensity, rhythm, timbre, tone, speed, strength, repetition, or pattern of the white, pink or brown noise. The device may use a speaker (or a combination of speakers) to generate the sleep entrainment beats, sleep entrainment rhythms and/or haptic vibrations.

Figure 12:
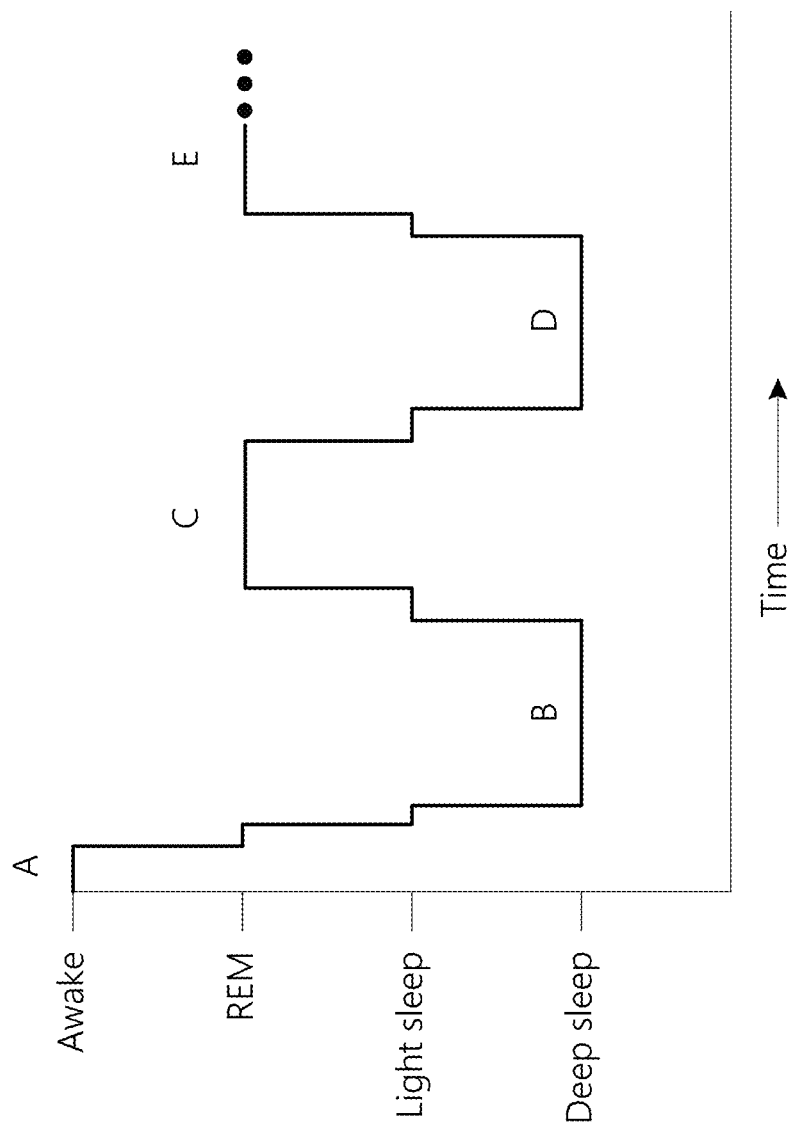
FIG. 12 is a chart depicting an example of a subject's sleep stages during sleep.

FIG. 12 depicts an example of a subject's sleep stages during sleep. At Time A, the subject is awake. At times B and D, the subject is in deep sleep. At times C and E, the subject is in REM sleep. At Time A, an accelerometer or a plurality of accelerometers such as is the embodiment depicted in FIG. 8A-8B or 9A-9B determines that the subject is awake. While the subject is determined to be awake, a device in or near a pillow of the subject may be activated to aid the subject in falling asleep. Any of the systems, devices or methods described above may aid the subject in falling asleep, and may include generating white, pink or brown noise and/or causing vibrations to stimulate a vagus nerve in the subject. At Times B and D, an accelerometer or a plurality of accelerometers such as is depicted in FIG. 8A-8B or 9A-9B are configured to determine that the subject is in deep sleep. While the subject is determined to be deep sleep, one or more of the systems, devices or methods may enhance deep sleep by any of the systems, devices or methods described above, such as, for example, DSB. Near the end of Time B or D, the enhancement of the subject's deep sleep may be ceased, or the stimulation may be changed or decreased, to allow the subject to enter light sleep or REM sleep. At Times B and D, a plurality of accelerometers such as is depicted in FIG. 8A-8B may determine that the subject is in REM sleep, and that the subject is not awake. While the subject is determined to be REM sleep, the subject may be unstimulated or otherwise allowed to remain in REM sleep for a period of time. For example, the plurality of accelerometers may determine that the subject is in REM sleep, and is not awake, and therefore, the subject may be allowed to remain in REM sleep instead of being stimulated or otherwise brought into a deep sleep state. At or near the end of Time C, the subject may be left unstimulated to naturally go back into light or deep sleep, or may be stimulated to enter a deep sleep state. At or near the end of Time E, the subject may be awakened, left unstimulated to awaken naturally or go naturally back into light or deep sleep, or be stimulated to enter a deep sleep state.

In some embodiments, a device with a plurality of accelerometers (such as is shown in FIG. 8A-8B) has improved function or works better than a device with a single accelerometer (such as is shown in FIG. 9A-9B) for differentiating whether a person is awake, in REM, in light sleep, and/or in deep sleep. In some embodiments, a device with a plurality of accelerometers in an array such as a 2×2 array (such as is shown in FIG. 8A-8B) has improved function over a device with a single accelerometer or a plurality of accelerometers that are not in an array (such as is shown in FIG. 9A-9B) for differentiating whether a person is awake, in REM, in light sleep, and/or in deep sleep. For example, a device plurality of accelerometers in an array such as a 2×2 array such as one depicted in FIG. 8A-8B may differentiate when a person is in REM as opposed to light sleep or awake by better resolving the person's movements, breathing, and/or heart rate. The device with the plurality of accelerometers in an array such as a 2×2 array may then induce deep sleep when it is sensed that the person is awake or in light sleep, but refrain from inducing deep sleep when the person is in REM.

On the other hand, a device with a single accelerometer such as one depicted in FIG. 9A-9B may detect movement data but be unable to resolve light sleep from REM and/or awake. This may result in the device inducing deep sleep during REM, for example. Thus, in some embodiments, the device prevents a person from entering REM. It may be desirable, however, to allow REM sleep to occur rather than maintain the person in deep sleep, as REM is part of a normal sleep pattern. Although in some embodiments a device with a single accelerometer may not be able to differentiate light sleep from REM sleep, the device with a single accelerometer may be configured to still allow REM to occur.

Some embodiments overcome difficulties differentiating light sleep vs. awake and/or deep sleep vs. REM sleep. For example, embodiments with plurality of accelerometers such as a 2×2 array of accelerometers are able to differentiate light sleep vs. awake and/or deep sleep vs. REM sleep, where some embodiments with a single accelerometer are unable to differentiate light sleep vs. awake and/or deep sleep vs. REM sleep. There could be one or more issues if these difficulties are not overcome. Such issues can include REM prevention that occurs when the device detects deep sleep, activates DSB, and continues playing DSB well into REM sleep, which has the same movement pattern as deep sleep. This issue may be reconciled by limiting the amount of time that DSB is able to play during any single bout of deep sleep, with a minimum delay before it can play again. In some embodiments, this feature is time-based and is independent of the sleep stage prediction algorithm. For example, some embodiments allow for 30 min of continuous DSB to play at most while the sleep stage prediction is deep sleep. In some embodiments, once this limit is reached, DSB is blocked from playing again (regardless of the sleep stage prediction) for a set period of time. In some embodiments, this delay period is when REM sleep is anticipated to occur since REM sleep typically follows a deep sleep bout of ~30 min.

In some embodiments, the device with a single accelerometer may be configured to allow REM to occur as follows: the device with a single accelerometer may detect a first movement or series of movements of the person and a second movement or series of movements of the person. When the device detects the first movement or series of movements, the device may induce deep sleep, but when the device detects the second movement or series of movements, the device may refrain from inducing deep sleep, thereby allowing the person to enter REM during or after the second movement or series of movements. A third series of movements detected by the accelerometer might then trigger the device to induce deep sleep, but when a fourth serious of movements is detected by the accelerometer the device might be configured to refrain from inducing deep sleep, thereby allowing the person to enter REM during or after the second movement or series of movements. This type of pattern could be programed into the device until a wake up window or a particular wake up time is reached, and the device no longer induces deep sleep so the person is allowed to wake up.

The following is an example of providing and integrating user feedback into a method, system, or device as provided herein. A user of a device that integrates movement data from accelerometer to predict sleep stages moves a lot during sleep, such that she is characterized by the device as in a light sleep stage when she is actually in a deep sleep stage. As a result, the device activates DSB to promote or enhance deep sleep in the subject less than is necessary to achieve a desired amount of deep sleep. The device transmits sleep data to the user's phone, where an application displays the amount of movement detected over time throughout the night, and also displays what sleep stages the user was characterized as being in at each time point, and when DSB was activated. The application presents an option to the user to adjust the threshold of what amount of movement data indicates each sleep stage of the user, or to adjust the amount of time DSB is activated. The user provides input to the application to decrease the sensitivity of the device, such that in future periods of sleep the device characterizes the user as in deep sleep even when an average user would have been characterized as in light sleep. The device activates DSB in periods when the device characterizes the user as in a deep sleep state, to enhance or promote deep sleep by playing a low frequency sound at 0.7 Hz to promote slow wave brain activity. The user also provides input to the application to limit the amount of time DSB is activated during future periods of sleep.

In another example, a subject obtains a DSB device that includes a plurality of accelerometers, a vibration source, and a sound source. The device is wirelessly connected to an application on the subject's mobile phone or computer. An application on the mobile phone or computer prompts the subject, through a display or through a speaker, to input whether the subject considers himself a light sleeper, a heavy sleeper, or an average sleeper. The subject indicates that he is a heavy sleeper. In response to the subject's input, the DSB device sets a threshold for determining whether the subject has entered deep sleep at a lower amount of movement than an average person. When the subject sleeps with the device, the plurality of accelerometers sense the subject's movement, determines that the subject has entered deep sleep, and activates DSB, including white noise or a low frequency tone at about 0.8 Hz, and vibration to stimulate the subject's vagus nerve.

Figure 15A:
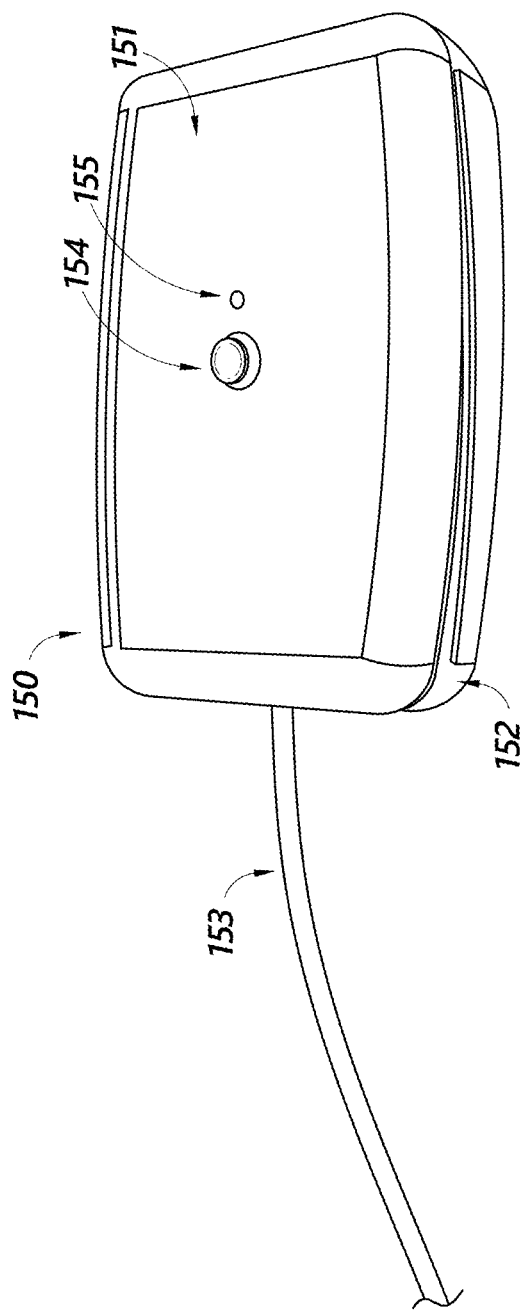
FIG. 15A depicts a sleep-aid device of an embodiment.
Figure 15B:
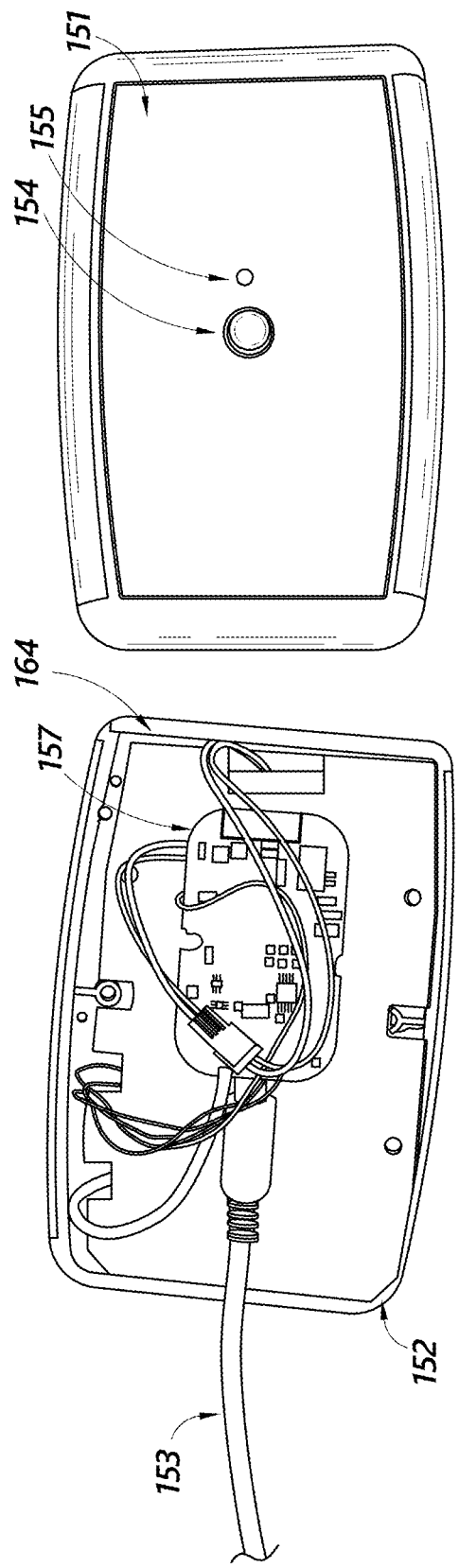
FIG. 15B depicts the device with the upper housing removed.
Figure 15C:
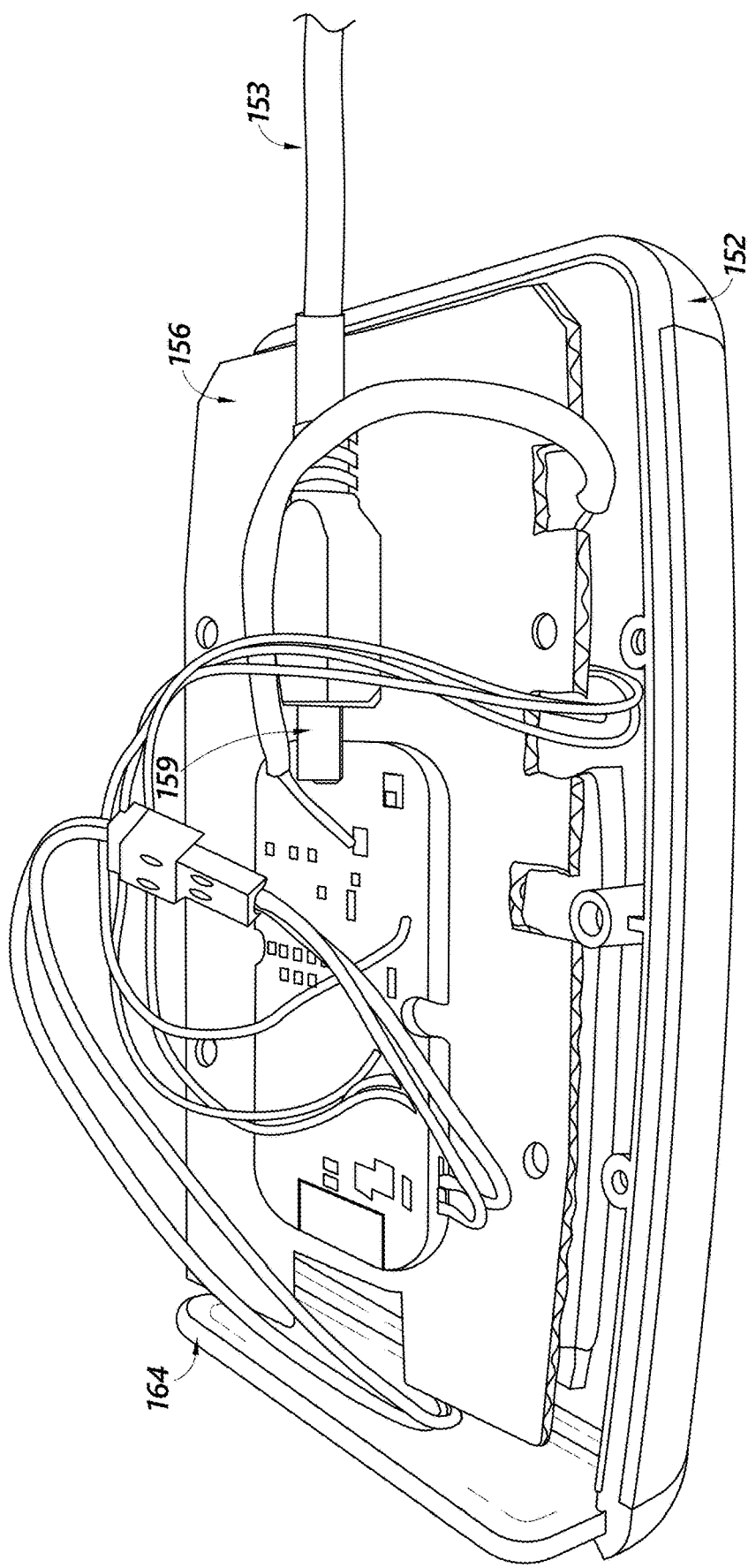
FIG. 15C depicts the upper electronics layer.
Figure 15D:
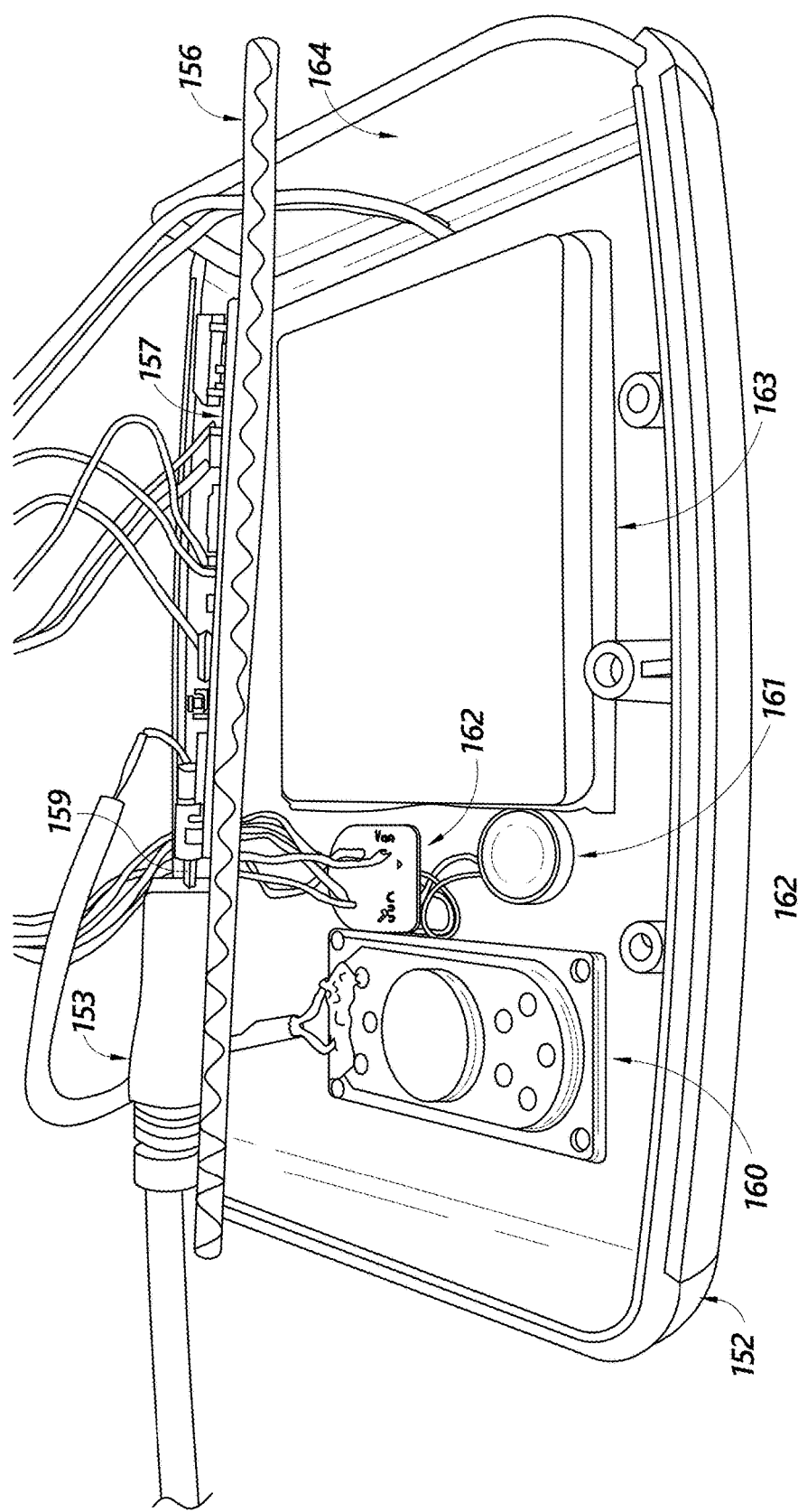
FIG. 15D depicts the lower electronics layer.

FIGS. 15A-D depict a device 150 of an embodiment. The device 150 of FIG. 15A includes an upper housing 151, a lower housing 152, and a cable 153 providing a connection between the device 150 and another device and/or a power source (not depicted, e.g., a wall charger, a battery pack, a sensor, and/or another device providing power and/or operational control). The upper housing 151 of the device 150 includes a button 154 for actuating the device and an aperture 155 through which an LED emits light indicative of operation of the device. FIG. 15B depicts the device 150 with the upper housing 151 removed, exposing side housing 164. In FIG. 15C, the upper electronics layer is shown separated from the lower electronics layer by a spacer 156. Atop the spacer 156 is situated a circuit board 157 including a processor (not depicted). The circuit board 157 is connected to the cable 153 via a USB mini connection 159. FIG. 15D depicts the lower electronics layer including a speaker 160 wired to the circuit board 157 and a vibrating motor disc 161 wired to a vibrating motor circuit board 162, which is in turn wired to the circuit board 157. A rechargeable lithium ion battery pack 163 is connected to the circuit board 157 and receives charging power from the cable 153 via the circuit board 157. Advantages of the depicted device, in addition to other advantages discussed elsewhere herein, include portability (capable of being held in a hand) and noninvasive to the user.

Example: Study on Synchronous Application of Aural Entrainment During Sleep

Introduction

The purpose of this research study was to test the effectiveness of the IO Sleep System (Chrona), which was created by Ultradia, a technology lifestyle company founded by WashU graduates. Chrona is a memory foam sensor sheet with embedded speakers, and that records movements during sleep. It analyzes sleep patterns based on this data, and selec2vely plays sleep and wake-enhancing sounds.

Background

Sleep problems may negatively impact health and productivity. Current solutions for sleep problems are largely pharmacological, and often cause myriad undesirable side-effects or long term complications. Non-invasive methods like acoustic intervention offer a readily accessible solution with similar benefits and less side effects. Slow wave sleep activity (SWA) has been identified as a marker of sleep which responds to acoustic stimulation.

Methods

Twenty three subjects were each invited to take 90 minute naps using Chrona at the EON lab while wearing EEG electrodes on their head, face, and arm. Each subject had two nap sessions, one experimental session and one control session. The study was double-blinded.

The experimental procedure was as follows: (1) pre-nap word-pair task, (2) nap using Chrona w/EEG, (3) mental subtraction task, and (4) post-nap word-pair task. EEG recordings were collected using Nihon Koden Polysmith sleep software. Recordings for one subject were compared to other recordings for that subject to assess the quality and duration of deep sleep. For the word-pair task, subjects were first shown a series of word pairs, then shown single words and asked to provide the complement. This test was used to compare cognitive function before and after nap the nap. Upon waking, each subject was instructed to perform a sequential subtraction task for a 3 minute period to assess ease of waking.

Results and Conclusions

The EEG results showed evidence of delta wave entrainment (a marker of deep sleep) using a rhythmic pattern at 2 Hz. Task data were separated into two groups: one from experimental trials, and one from control trials. An analysis of pre vs. post nap task scores shows a ~2% difference in accuracy between experimental and control groups (see Table 1). These data and results indicate that Chrona, as well as the other embodiments described herein, are valid for improving deep sleep.

TABLE 1

| | Average: | | |
| --- | --- | --- | --- |
| | Pre-nap accuracy | Post-nap accuracy | Change in accuracy |
| Group 1 | 72% | 69% | 4.5% |
| Group 2 | 69% | 67% | 2.0% |

Exemplary Devices and Methods

Method 1: A sleep-aid device, comprising: a speaker, optionally situated on or in a pillow, adapted to generate white, pink, and/or brown noise or a low-frequency tone, the white, pink and/or brown noise or the low-frequency tone being configured to stimulate a vagus nerve of a subject, optionally when a head of the subject is on the pillow; a monaural tone generator; a processor electronically connected to the monaural tone generator, the processor having software code configured to generate a monaural tone from the monaural tone generator based on detected physical signs which approximate a sleep stage or a depth of sleep; and a sensor electronically connected to the processor, the sensor receiving detected physical signs from the subject of one or more of movement data, heart rate and respiration rate, wherein a combination of the software code and the processor are adapted to differentiate a deep sleep stage of the subject from a REM sleep stage of the subject based on sequence and timing of the detected physical signs.

Method 2: The sleep-aid device of Method 1, further comprising one or more of a battery, an accelerometer, a memory, and a wired or wireless connection adapted for communication with a smartphone.

Method 3: The sleep-aid device of Method 2, wherein the wired or wireless connection adapted for communication with the smartphone is wired.

Method 4: The sleep-aid device of Method 2, wherein the wired or wireless connection adapted for communication with the smartphone is wireless.

Method 5: The sleep-aid device of Method 2, wherein the wired or wireless connection adapted for communication with the smartphone is Bluetooth.

Method 6: The sleep-aid device of any of Methods 1-5, further comprising a termination sequence activated by one or more of a predetermined timer, movement data, heart rate, and respiration data.

Method 7: The sleep-aid device of any of Methods 1-6, further comprising a vibration motor, wherein the vibration motor comprises a strap.

Method 8: The sleep-aid device of any of Methods 1-7, wherein the monaural tone is white, pink or brown noise.

Method 9: The sleep-aid device of any of Methods 1-8, further comprising a plurality of accelerometers.

Method 10: The sleep-aid device of Method 9, wherein the plurality of accelerometers comprises accelerometers arranged in a 2×2 matrix layout in relation to each other.

Method 11: The sleep-aid device of any of Methods 1-10, further comprising one or more of Deep Sleep Boost™ and Gentle Wake-up™ technology.

Method 12: A method for inducing or modifying sleep in a subject, comprising: activating a device in or near a pillow; generating a white, a pink or a brown noise through the device; causing the device to produce low-frequency tones; and stimulating a vagus nerve to induce sleep in a subject.

Method 13: The sleep-aid device of Method 12, further comprising connecting the device to a smartphone.

Method 14: The sleep-aid device of Method 13, wherein a connection of the device to the smartphone is wireless.

Method 15: The sleep-aid device of Method 13 or 14, wherein stimulating the vagus nerve is accomplished by vibrations, the method further comprising controlling, via the smartphone, the white, the pink, or the brown noise and/or the vibrations.

Method 16: The sleep-aid device of Method 15, wherein controlling the low-frequency tones comprises controlling a speed, a strength, a rhythm, a repetition, or a pattern of the tones.

Method 17: The sleep-aid device of Method 15 or 16, wherein controlling the white, pink or brown noise comprises controlling a pitch, a frequency, a period, a loudness, a volume, an amplitude, an intensity, a rhythm, a timbre, a tone, a speed, a strength, a repetition, or a pattern of the white, the pink, or the brown noise.

Method 18: The sleep-aid device of any of Methods 12-17, wherein stimulating the subject's vagus nerve decreases the subject's heart rate and/or respiration rate.

Method 19: The sleep-aid device of any of Methods 12-18, further comprising measuring the subject's body movement, head movement, respiration rate, or heart rate with a plurality of accelerometers.

Method 20: The sleep-aid device of any of Methods 12-19, further comprising generating sleep entrainment beats or haptic vibrations through the device.

Method 21: The sleep-aid device of Method 20, wherein the device uses one or more speakers to generate the sleep entrainment beats or haptic vibrations.

Method 22: A method for differentiating deep sleep stages from REM sleep stages, comprising: receiving movement data from a device near a sleeping subject; calculating movements of the sleeping subject over time; and designating every other time-sequence of relatively low-movement data as REM sleep with a deep sleep always as a first time-sequence.

Method 23: The sleep-aid device of Method 22, further comprising connecting the device to a smartphone.

Method 24: The sleep-aid device of Method 23, wherein connecting is wirelessly connecting.

Method 25: The sleep-aid device of Method 23 or 24, further comprising generating a white, a pink or a brown noise through the device and generating vibrations to stimulate the vagus nerve, the method further comprising controlling, via the smartphone, the white, the pink or the brown noise or the vibrations.

Method 26: The sleep-aid device of Method 25, further comprising generating low frequency tones, wherein controlling the low-frequency tones comprises controlling a speed, a strength, a rhythm, a repetition, or a pattern of the low-frequency tones.

Method 27: The sleep-aid device of Method 25 or 26, wherein controlling the white, the pink or the brown noise comprises controlling a pitch, a frequency, a period, a loudness, a volume, an amplitude, an intensity, a rhythm, a timbre, a tone, a speed, a strength, a repetition, or a pattern of the white, the pink or the brown noise.

Method 28: The sleep-aid device of any of Methods 22-27, further comprising generating a vibration through the device to stimulate the vagus nerve, wherein stimulating the subject's vagus nerve decreases the subject's heart rate or respiration rate.

Method 29: The sleep-aid device of any of Methods 22-28, further comprising measuring the subject's respiration rate or heart rate with a plurality of accelerometers.

Method 30: The sleep-aid device of any of Methods 22-29, further comprising generating sleep entrainment beats or haptic vibrations through the device.

Method 31: The sleep-aid device of Method 30, wherein the device uses one or more speakers to generate the sleep entrainment beats or haptic vibrations.

System 32: A system for inducing or modifying sleep in a subject, comprising: a speaker; and an accelerometer configured to be placed on a first side of a pillow configured to receive a subject's head with a second side of the pillow opposite the first side of the pillow.

System 33: The system of System 32, further comprising a strap configured to connect the speaker or the accelerometer to the pillow.

System 34: The system of System Error! Reference source not found., wherein the strap is configured to wrap around the pillow vertically in relation to the subject's neck.

System 35: The system of System Error! Reference source not found. or Error! Reference source not found., wherein the strap comprises a flexible fabric.

System 36: The system of System Error! Reference source not found.—Error! Reference source not found., wherein the speaker is configured for placement adjacent to or next to the pillow.

System 37: A system for inducing sleep in a subject, comprising: a speaker; and four accelerometers configured to be arranged in a 2×2 matrix formation on a second side of a pillow opposite a first side of the pillow configured to receive a subject's head.

System 38: The system of System Error! Reference source not found., further comprising a strap configured to connect the speaker or the four accelerometers to the pillow.

System 39: The system of System Error! Reference source not found., wherein the strap is configured to wrap vertically in relation to the subject's neck, around the pillow.

System 40: A system for differentiating between a deep sleep stage and a REM sleep stage in a subject, comprising: a pillow having a first side configured to receive a subject's head and a second side opposite the first side; an accelerometer in physical contact with the pillow; and a processor electrically connected to the accelerometer, the processor configured to receive detected physical signs of the subject of one or more of movement data, heart rate, and respiration rate from the accelerometer, and the processor configured to differentiate a deep sleep stage from a REM sleep stage based on a sequence and a timing of the detected physical signs.

System 41: The system of System 40, further comprising a strap connecting the accelerometer to the pillow.

System 42: The system of System 41, wherein the strap is wrapped around the pillow vertically in relation to the subject's neck.

System 43: The system of System 41 or 42, wherein the strap comprises a flexible fabric.

System 44: The system of any of Systems 41-43, wherein the speaker is in proximity to, adjacent to, in, under, or atop the pillow.

System 45: A system for differentiating between deep sleep and REM sleep stages in a subject, comprising: a pillow having a first side configured to receive a subject's head and a second side opposite the first side; four accelerometers arranged in a 2×2 matrix formation on the second side of the pillow; and a processor wired or wirelessly connected to the four accelerometers.

System 46: The system of System 45, further comprising a strap connecting the four accelerometers to the pillow.

System 47: A method for providing Deep Sleep Boost™ (DSB) to a subject, comprising: sensing, by an accelerometer, movement of a subject during a first sleep period; determining, based on both the sensed movement of the subject and a predetermined threshold amount of movement, a sleep state of the subject throughout the first sleep period; displaying information about the subject's movement sensed during the first sleep period, and information about the sleep state determined during the first sleep period; obtaining input from the subject to increase or decrease the predetermined threshold amount of movement to set a second threshold amount of movement; and activating DSB during a second sleep period based on the second threshold amount of movement.

System 48: The system of System 47, further comprising obtaining input from the subject to limit the amount of time that DSB is activated during the second sleep period.

Method 49: A method for providing Deep Sleep Boost™ (DSB) to a subject, comprising: obtaining input from a subject, through a device, about whether the subject is considered a light sleeper, a deep sleeper, or an average sleeper, or about whether the subject moves around more than average, less than average, or an average amount during sleep; determining, based on the obtained input, a threshold amount of movement for determining a sleep state of the subject; sensing, by an accelerometer, movement of a subject during a sleep period; determining, based on both the sensed movement of the subject and the determined threshold amount of movement, a sleep state of the subject throughout the sleep period; and activating DSB during the sleep period based on the determined sleep state.

Method 50: The method of Method 49, wherein determining a threshold amount of movement for determining a sleep state of the subject comprises adjusting a predetermined threshold based on the obtained input.

Device 51: A sleep-aid device, comprising: an upper housing; a lower housing; a side housing; a spacer; an upper electronics layer comprising: a circuit board comprising a processor, and a USB micro connector; and a lower electronics layer comprising: a speaker secured to the lower housing and wired to the circuit board, the speaker adapted to generate a white, a pink, and/or a brown noise or a low-frequency tone, the white, pink and/or brown noise, a vibrating motor circuit board, a vibrating motor secured to the lower housing and wired to the vibrating motor circuit board, the vibrating motor adapted to generate a vibration adapted to stimulate a vagus nerve of a subject, and a rechargeable lithium ion battery pack wired to the circuit board, wherein the upper housing, the lower housing, and the side housing cooperate to enclose the upper electronics layer, the lower electronics layer and the spacer, wherein the spacer physically separates the upper electronics layer from the lower electronics layer, wherein the USB micro connector is adapted to receive a cable extending through an aperture between the upper housing and the lower housing, and to provide an electrical connection and/or a data connection between the device and a power source, a sensor, and/or a computing device, and wherein the processor is adapted to receive detected physical signs of a subject of one or more of movement data, heart rate, and respiration rate from an accelerometer, to differentiate a deep sleep stage from a REM sleep stage in a sleep period based on a sequence and a timing of the detected physical signs, and to actuate the speaker and/or the vibrating motor during the sleep period based on the determined sleep state.

The disclosure is generally described herein using affirmative language to describe the numerous embodiments. The disclosure also includes embodiments in which subject matter is excluded, in full or in part, such as substances or materials, method steps and conditions, protocols, or procedures.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). The term "comprising" as used herein is synonymous with 'including,' 'containing,' or 'characterized by,' and is inclusive or open-ended and does not exclude additional, unrecited elements or method steps. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

In addition, where features or aspects of the disclosure are described in terms of Markush groups, those skilled in the art will recognize that the disclosure is also thereby described in terms of any individual member or subgroup of members of the Markush group. To the extent publications and patents or patent applications incorporated by reference contradict the disclosure contained in the specification, the specification is intended to supersede and/or take precedence over any such contradictory material.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor, memory, or other unit may fulfill the functions of several items recited in the claims. The mere fact that certain items or features are recited in mutually different dependent claims does not indicate that a combination of these items or features cannot be used to advantage. Any reference signs in the claims should not be construed as limiting the scope.

All numbers expressing quantities, dimensions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A sleep-aid device, comprising:
   a strap configured to be positioned around a pillow;
   at least one sensor positioned on or within the strap, the at least one sensor configured to receive detected physical signs of one or more of movement data, heart rate, and respiration rate from a subject; and
   a device configured to be secured to the pillow by the strap, the device comprising:
      a speaker; and
      a processor electronically connected to the speaker and the at least one sensor, the processor having software code configured to:
         cause the speaker to play one or more user-selected audio files,
         detect, based on the detected physical signs received from the at least one sensor, a sleep state of the subject, and
         upon determination that the sleep state of the subject indicates that the subject is in a deep sleep state:
            cause the speaker to stop playing the one or more user-selected audio files, and
            cause the speaker to generate a constant monaural tone from the speaker, wherein the constant monaural tone has a frequency of less than 1 Hz, wherein the speaker plays the monaural tone while the subject remains in the deep sleep state and for at most 30 minutes.

2. The sleep-aid device of claim 1, wherein the device configured to be secured to the pillow by the strap further comprises one or more of a battery, an accelerometer, a memory, and a wired or wireless connection adapted for communication with a smartphone.

3. The sleep-aid device of claim 2, wherein the wired or wireless connection adapted for communication with the smartphone is wired.

4. The sleep-aid device of claim 2, wherein the wired or wireless connection adapted for communication with the smartphone is wireless.

5. The sleep-aid device of claim 1, further comprising a termination sequence activated by one or more of a predetermined timer, movement data, heart rate, and respiration data.

6. The sleep-aid device of claim 1, further comprising a vibration motor.

7. The sleep-aid device of claim 1, wherein the monaural tone is white, pink or brown noise.

8. The sleep-aid device of claim 1, wherein the at least one sensor comprises one or more accelerometers.

9. The sleep-aid device of claim 8, wherein the one or more accelerometers comprise a plurality of accelerometers arranged in a 2×2 matrix layout in relation to each other.

10. The sleep-aid device of claim 1, wherein the monaural tone has a frequency of about 0.8 Hz.

11. The sleep-aid device of claim 1, wherein the processor is configured to cause the speaker to stop playing the one or more audio files and to generate the monaural tone upon determination that the sleep state of the subject indicates that the user is in a light sleep stage or a REM sleep stage.

12. The sleep-aid device of claim 1, wherein the deep sleep state comprises a phase of sleep with slow wave brain activity within a frequency range of 0.5 Hz to 2 Hz and low physical movement.

* * * * *